(12) United States Patent
Huang et al.

(10) Patent No.: US 12,405,213 B2
(45) Date of Patent: Sep. 2, 2025

(54) RAPID ESTIMATION OF A SOIL-WATER RETENTION CURVE USING VISIBLE-NEAR INFRARED SPECTROSCOPY

(71) Applicant: Wisconsin Alumni Research Foundation, Madison, WI (US)

(72) Inventors: Jingyi Huang, Madison, WI (US); Zampela Pittaki-Chrysodonta, Madison, WI (US); Alfred Hartemink, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 211 days.

(21) Appl. No.: 17/833,543

(22) Filed: Jun. 6, 2022

(65) Prior Publication Data

US 2022/0397523 A1 Dec. 15, 2022

Related U.S. Application Data

(60) Provisional application No. 63/196,830, filed on Jun. 4, 2021.

(51) Int. Cl.
| | | |
|---|---|---|
| *G01N 21/35* | (2014.01) | |
| *G01N 21/3554* | (2014.01) | |
| *G01N 21/359* | (2014.01) | |
| *G01N 33/24* | (2006.01) | |

(52) U.S. Cl.
CPC ....... *G01N 21/3554* (2013.01); *G01N 21/359* (2013.01); *G01N 33/246* (2013.01); *G01N 33/245* (2024.05)

(58) Field of Classification Search
CPC ............ G01N 21/3554; G01N 21/359; G01N 33/246; G01N 33/245; G01N 2021/8405; G01N 2201/129; G01N 21/31
See application file for complete search history.

(56) References Cited

U.S. PATENT DOCUMENTS

| | | | | |
|---|---|---|---|---|
| 2005/0114101 | A1* | 5/2005 | Hatfield | ............... G01N 21/274 703/2 |
| 2016/0139021 | A1* | 5/2016 | Stroock | ............... G01N 33/246 73/73 |
| 2017/0122889 | A1* | 5/2017 | Weindorf | ............. G01N 21/359 |
| 2018/0003608 | A1* | 1/2018 | Stroock | .................. G01N 13/02 |
| 2018/0172659 | A1* | 6/2018 | Visser | ................... G01N 33/24 |
| 2022/0397523 | A1 | 12/2022 | Huang et al. | |

OTHER PUBLICATIONS

Babaeian, E. et al., 2015. A comparative study of multiple approaches for predicting the soil-water retention curve: hyperspectral information vs. basic soil properties. Soil Sci Soc Am J, 79(4): 1043-1058. DOI: 10.2136/sssaj2014.09.0355.

(Continued)

*Primary Examiner* — Alvaro E Fortich
(74) *Attorney, Agent, or Firm* — Quarles & Brady, LLP

(57) ABSTRACT

Disclosed are methods and systems for accurate modeling of the soil-water retention curve (SWRC) for any soil texture class and with varying amounts of soil organic matter. The disclosed method leverages near-visible infrared spectroscopy (vis-NIRS) to obtain rapid measurements at low soil-water potential that are used to model soil-water retention functions.

18 Claims, 9 Drawing Sheets

(56) References Cited

OTHER PUBLICATIONS

Barnes, R.J., Dhanoa, M.S., Lister, S.J., 1989. Standard normal variate transformation and detrending of near-infrared diffuse reflectance spectra. Appl Spectrosc, 43(5): 772-777. DOI:10.1366/0003702894202201.

Bishop, J.L., Pieters, C.M., Edwards, J.O., 1994. Infrared spectroscopic analyses on the nature of water in montmorillonite. Clay Clay Miner, 42(6): 702-716. DOI:10.1346/CCMN.1994.0420606.

Blaschek, M., Roudier, P., Poggio, M., Hedley, C.B., 2019. Prediction of soil available water-holding capacity from visible near-infrared reflectance spectra. Sci Rep-Uk, 9(1): 12833-12833. DOI:10.1038/s41598-019-49226-6.

Brooks, R.H. and Corey, A.T., 1964. Hydraulic properties of porous media. Hydrology Paper No. 3. Civil Engineering Dep., Colorado State Univ., Fort Collins, CO.

Campbell, G., Shiozawa, S., 1989. Prediction of hydraulic properties of soils using particle-size distribution and bulk density data. Indirect methods for estimating the hydraulic properties of unsaturated soils: 317-328.

Campbell, G.S., 1974. Simple method for determining unsaturated conductivity from moisture retention data. Soil Science, 117(6): 311-314. DOI:10.1097/00010694-197406000-00001.

Clapp, R.B., Hornberger, G.M., 1978. Empirical equations for some soil hydraulic-properties. Water Resour Res, 14(4): 601-604. DOI:10.1029/WR014i004p00601.

de Jong, S., 1993. Simpls—an alternative approach to partial least-squares regression. Chemometr Intell Lab, 18(3): 251-263. DOI: 10.1016/0169-7439(93)85002-X.

Galvao, L.S., Vitorello, I., 1998. Variability of laboratory measured soil lines of soils from southeastern Brazil. Remote Sens Environ, 63(2): 166-181. DOI:10.1016/S0034-4257(97)00135-1.

Gowen, A.A., Downey, G., Esquerre, C., O'Donnell, C.P., 2011. Preventing over-fitting in PLS calibration models of hear-infrared (NIR) spectroscopy data using regression coefficients. J Chemometr, 25(7): 375-381. DOI:10.1002/cem.1349.

Gupta, S.C., Larson, W.E., 1979. Estimating soil-water retention characteristics from particle-size distribution, organic-matter percent, and bulk-density. Water Resour Res, 15(6): 1633-1635. DOI:10.1029/WR015i006p01633.

Hunt, G.R., 1977. Spectral signatures of particulate minerals in visible and near infrared. Geophysics, 42(3): 501-513. DOI:10.1190/1.1440721.

Jarvis, N.J., Messing, I., Larsson, M.H., Zavattaro, L., 1999. Measurement and prediction of near-saturated hydraulic conductivity for use in dual-porosity models, In: van Genuchten, M.T., Leij, F.J., Wu, L. (Eds.). Characterization and measurement of the hydraulic properties of unsaturated porous media (Riverside, CA, USA: Oct. 22-24, 1997), pp. 839-850.

Jensen, D.K., Tuller, M., de Jonge, L.W., Arthur, E., Moldrup, P., 2015. A new two-stage approach to predicting the soil water characteristic from saturation to oven-dryness. J Hydrol, 521:498-507. DOI:10.1016/j.jhydrol.2014.12.018.

Karup, D., Moldrup, P., Tuller, M., Arthur, E., de Jonge, L.W., 2017. Prediction of the soil water retention curve for structured soil from saturation to oven-dryness. Eur J Soil Sci, 68(1): 57-65. DOI:10.1111/ejss.12401.

Kilmer, V.J., Alexander, L.T., 1949. Methods of making mechanical analyses of soils. Soil Science, 68(1): 15-24. DOI:10.1097/00010694-194907000-00003.

Klute, A., 1986. Water retention: Laboratory methods. In A. Klute (ed.) Methods of soil analysis. Part 1. Physical and mineralogical methods. 2nd ed. Agron. Monogr. 9. ASA and SSSA, Madison, WI, 5: 635-662.

Mader, D.L., 1963. Soil Variability—A Serious Problem in Soil-Site Studies in the Northeast. Soil Science Society of America Journal, 27(6): 707-709. DOI:10.2136/sssaj1963.03615995002700060040x.

McDowell, M.L., Bruland, G.L., Deenik, J.L., Grunwald, S., Knox, N.M., 2012. Soil total carbon analysis in Hawaiian soils with visible, near-infrared and mid-infrared diffuse reflectance spectroscopy. Geoderma, 189-190: 312-320. DOI:10.1016/j.geoderma.2012.06.009.

Moldrup, P., Olesen, T., Komatsu, T., Schjonning, P., Rolston, D.E., 2001. Tortuosity, diffusivity, and permeability in the soil liquid and gaseous phases. Soil Sci Soc Am J, 65(3): 613-623. DOI:10.2136/sssaj2001.653613x.

Nielsen, D.R., Biggar, J.W., Erh, K.T., 1973. Spatial variability of field-measured soil-water properties. Hilgardia, 42: 215-259. DOI:10.3733/hilg.v42n07p215.

Norris, K., 2001. Applying norris derivatives. Understanding and correcting the factors which affect diffuse transmittance spectra. NIR news, 12(3): 6-9. DOI: 10.1255/nim.613.

Olesen, T., Moldrup, P., Henriksen, K., Petersen, L.W., 1996. Modeling diffusion and reaction in soils .4. New models for predicting ion diffusivity. Soil Science, 161(10): 633-645. DOI:10.1097/00010694-199610000-00001.

Or, D., Tuller, M., 1999. Liquid retention and interfacial area in variably saturated porous media: Upscaling from single-bore to sample-scale model. Water Resour Res, 35(12): 3591-3605. DOI:10.1029/1999wr900262.

Oswin, C.R., 1946. The kinetics of package life. III. The isotherm. Journal of the Society of Chemical Industry, 65(12): 419-421. DOI:10.1002/jctb.5000651216.

Pachepsky, Y., Rawls, W.J., Giménez, D., 2001. Comparison of soil water retention at field and laboratory scales. Soil Sci Soc Am J, 65(2): 460-462. DOI:10.2136/sssaj2001.652460x.

Peck, A.J., Luxmoore, R.J., Stolzy, J.L., 1977. Effects of spatial variability of soil hydraulic properties in water budget modeling. Water Resources Research, 13(2): 348-354. DOI:10.1029/WR013i002p00348.

Pham, H.Q., Fredlund, D.G., 2008. Equations for the entire soil-water characteristic curve of a volume change soil. Can Geotech J, 45(4): 443-453. DOI:10.1139/T07-117.

Pittaki-Chrysodonta, Z. et al., 2019. Comparing visible-near-infrared spectroscopy and a pedotransfer function for predicting the dry region of the soil-water retention curve. Vadose Zone J, 18(1). DOI:10.2136/vzj2018.09.0180.

Pittaki-Chrysodonta, Z., Hartemink, A.E., Sanderman, J., Ge, Y., Huang, J., 2021. Evaluating three calibration transfer methods for predictions of soil properties using mid-infrared spectroscopy. Soil Sci Soc Am J, n/a(n/a). DOI: 10.1002/saj2.20225.

Pittaki-Chrysodonta, Z. et al., 2018. Predicting the Campbell soil water retention function: Comparing visible-near-infrared spectroscopy with classical pedotransfer function. Vadose Zone J, 17(1). DOI:10.2136/vzj2017.09.0169.

Rawls, W.J., Brakensiek, D.L., Saxton, K.E., 1982. Estimation of soil water properties. T Asae, 25(5). DOI:10.13031/2013.33720.

Rinnan, A., Berg, F.v.d., Engelsen, S.B., 2009. Review of the most common pre-processing techniques for near-infrared spectra. TrAC Trends in Analytical Chemistry, 28(10): 1201-1222. DOI:10.1016/j.trac.2009.07.007.

Rossi, C., Nimmo, J.R., 1994. Modeling of soil-water retention from saturation to oven dryness. Water Resour Res, 30(3): 701-708. DOI:10.1029/93wr03238.

Santra, P. et al., 2009. Estimation of soil hydraulic properties using proximal spectral reflectance in visible, near-infrared, and shortwave-infrared (VIS-NIR-SWIR) region. Geoderma, 152(3-4): 338-349. DOI:10.1016/j geoderma.2009.07.001.

Savitzky, A., Golay, M.J.E., 1964. Smoothing and differentiation of data by simplified least squares procedures. Anal Chem, 36(8): 1627-1639. DOI:10.1021/ac60214a047.

Schaap, M.G., Leij, F.J., van Genuchten, M.T., 1998. Neural network analysis for hierarchical prediction of soil hydraulic properties. Soil Sci Soc Am J, 62(4): 847-855. DOI:10.2136/sssaj1998.03615995006200040001x.

Schaap, M.G., Leij, F.J., van Genuchten, M.T., 2001. Rosetta: a computer program for estimating soil hydraulic parameters with hierarchical pedotransfer functions. J Hydrol, 251(3): 163-176. DOI:10.1016/S0022-1694(01)00466-8.

Seybold, C.A. et al., 2019. Application of mid-infrared spectroscopy in soil survey. Soil Sci Soc Am J, 83(6): 1746-1759. DOI:10.2136/sssaj2019.06.0205.

(56) References Cited

OTHER PUBLICATIONS

Sharma, M.L., Uehara, G., 1968. Influence of soil structure on water relations in low humic latosols .I. Water retention. Soil Sci Soc Am Pro, 32(6): 765-&. DOI:10.2136/sssaj1968.03615995003200060021x.

Silva, A.C.d., Armindo, R.A., Minasny, B., Prevedello, C.L., 2021. Evaluating the Splintex model for estimating the soil water retention curve for a wide range of soils. Soil and Tillage Research, 209: 104974. DOI:10.1016/j.still.2021.104974.

Sjöblom, J., Svensson, O., Josefson, M., Kullberg, H., Wold, S., 1998. An evaluation of orthogonal signal correction applied to calibration transfer of near infrared spectra. Chemometr Intell Lab, 44(1): 229-244. DOI:10.1016/S0169-7439(98)00112-9.

Stenberg, B., Rossel, R.A.V., Mouazen, A.M., Wetterlind, J., 2010. Visible and near infrared spectroscopy in soil science. Adv Agron, 107: 163-215. DOI:10.1016/S0065-2113(10)07005-7.

van den Berg, C., Bruin, S., 1981. Water activity and its estimation in food systems: theoretical aspects. In: Rockland, L.B., Stewart, G.F. (Eds.), Water activity: Influences on food quality. Academic Press, New York, pp. 147-177.

van Genuchten, M.T., 1980. A closed-form equation for predicting the hydraulic conductivity of unsaturated soils. Soil Science Society of America Journal, 44(5): 892-898. DOI:10.2136/sssaj1980.03615995004400050002x.

Varvaris, I., Børgesen, C.D., Kjærgaard, C., Iversen, B.V., 2018. Three two-dimensional approaches for simulating the water flow dynamics in a heterogeneous tile-drained agricultural field in Denmark. Soil Science Society of America Journal, 82(6): 1367-1383. DOI:10.2136/sssaj2018.05.0190.

Varvaris, I., Pittaki-Chrysodonta, Z., Børgesen, C.D., Iversen, B.V., 2020. Parameterization of two-dimensional approaches in HYDRUS-2D. Part 1: for simulating water flow dynamics in catchment scale. In review. . Soil Science Society of America Journal.

Varvaris, I., Pittaki-Chrysodonta, Z., Moldrup, P., De Jonge, L.W., Iversen, B.V., 2019. Combining visible-near-infrared and pedotransfer functions for parameterization of tile drain flow simulations. Vadose Zone Journal, 18(1). DOI:10.2136/vzj2018.09.0171.

Viscarra Rossel, R.A., Walvoort, D.J.J., McBratney, A.B., Janik, L.J., Skjemstad, J.O., 2006. Visible, near infrared, mid Infrared or combined diffuse reflectance spectroscopy for simultaneous assessment of various soil properties. Geoderma, 131(1/2): 59-75. DOI:10.1016/j.geoderma.2005.03.007.

Wetterlind, J., Stenberg, B., Viscarra Rossel, R.A., 2013. Soil analysis using visible and near infrared spectroscopy. Methods in molecular biology (Clifton, N.J.), 953: 95-107. DOI:10.1007/978-1-62703-152-3_6.

Williams, J., Prebble, R.E., Williams, W.T., Hignett, C.T., 1983. The influence of texture, structure and clay mineralogy on the soil-moisture characteristic. Aust J Soil Res, 21(1): 15-32. DOI:10.1071/Sr9830015.

Williams, J., Ross, P., Bristow, K.L., 1989. Prediction of the Campbell water retention function from texture, structure, and organic matter, In: van Genuchten, M Th. and Leij, F J (eds.). Proceedings of the International Workshop on Indirect Methods for Estimating the Hydraulic Properties of Unsaturated Soils (Riverside, CA, USA: Oct. 11-13, 1989), pp. 427-441.

Wood, E.F., Sivapalan, M., Beven, K., Band, L., 1988. Effects of spatial variability and scale with implications to hydrologic modeling. Journal of Hydrology, 102(1): 29-47. DOI:10.1016/0022-1694(88)90090-X.

Wosten, J.H.M., Pachepsky, Y.A., Rawls, W.J., 2001. Pedotransfer functions: bridging the gap between available basic soil data and missing soil hydraulic characteristics. J Hydrol, 251(3): 123-150. DOI:10.1016/S0022-1694(01)00464-4.

\* cited by examiner

RAPID ESTIMATION OF A SOIL-WATER RETENTION CURVE USING VISIBLE-NEAR INFRARED SPECTROSCOPY

CROSS-REFERENCE TO RELATED APPLICATIONS

This application claims the benefit of priority under 35 U.S.C. § 119(e) of U.S. Provisional Application No. 63/196,830, filed Jun. 4, 2021, the contents of which are incorporated herein by reference in its entirety.

STATEMENT REGARDING FEDERALLY SPONSORED RESEARCH OR DEVELOPMENT

Not applicable.

FIELD OF INVENTION

The field of the invention relates to the use of near visible-infrared (vis-NIRS) spectroscopy to model the soil-water retention curve (SWRC).

BACKGROUND

Soil-water retention (SWR) describes the relationship between soil moisture content and soil-water potential (i.e., the amount of water retained by the soil at a specific soil-water potential). Typically, an SWR curve (or function) is used to predict the soil water availability, the field capacity (water supply to plants), and soil aggregate stability. As a result, SWR curves are a key input for hydrogeological models used in a variety of disciplines and applications.

Unfortunately, the lack of high-quality soil data and the spatial variability of soil properties within a field lead to large uncertainties in the hydrogeological models. Further, measuring the soil-water retention curve (SWRC) in a laboratory, for a particular soil source (e.g., particular field), requires specialized equipment, standardized procedures, environmental controls, and technical staff. In addition, laboratory analysis requires field collection and temperature-controlled storage of the samples. These factors cause traditional laboratory analysis of SWRCs to be costly and time-consuming. As a result, a limited number of soil samples are typically analyzed, reducing the potential accuracy of the SWRCs.

After analysis of the raw samples, a function is fit to the empirically derived soil-water retention (SWR) data. Several semi-physical and empirical models have been proposed for fitting the SWR data (e.g. Brooks & Corey, 1964; Campbell, 1974; van Genuchten, 1980). For example, the Campbell (1974) soil-water retention function requires only information of a curve shape parameter (the pore-size distribution parameter, Campbell b) and the maximum amount of water that can be retained from the soil (saturated water content—$\theta_s$).

SUMMARY OF THE INVENTION

Disclosed herein are several non-limiting illustrative embodiments of the present technology, which generally relates to methods and systems for characterizing soil, using spectrographic data.

In a first aspect of the disclosure, methods of characterizing soil are provided. In some embodiments, the methods comprise: receiving, with one or more computing devices, spectroscopy data for a soil sample; determining a first model parameter for a soil-water retention function; and characterizing the soil sample based on the soil-water retention function wherein the first model parameter provides an anchor value for the soil-water retention curve; and wherein the anchor value corresponds to a water potential of potential force (pF) at least between 3.8 and 4.2, inclusive. In some embodiments, the soil-water retention function is a Campbell soil-water retention function. In some embodiments, the methods further comprise: determining, a second model parameter for the soil-water retention function, based on the spectroscopy data, wherein the second model parameter is an exponential shape factor. In some embodiments, the anchor value corresponds to a water potential of pF at least 4.2. In some embodiments, the methods further comprise: receiving a soil sample; and conducting a spectroscopy analysis of the soil sample to obtain the spectroscopy data. In some embodiments, the spectroscopy analysis includes vis-NIR spectroscopy analysis. In some embodiments, the soil sample is an air-dried, sieved soil sample. In some embodiments, the soil sample is a core sample. In some embodiments, the first model parameter is determined with the one or more computing devices based on the spectroscopy data. In some embodiments, the first model parameter is empirically determined.

In another aspect of the current disclosure, systems for characterizing soil are provided. In some embodiments, the systems comprise: a spectrophotometer configured to receive a soil sample and provide spectroscopy data for the soil sample; and one or more computing devices configured to: receive the spectroscopy data for the soil sample from the spectrophotometer; determine a first model parameter for a soil-water retention function, the first model parameter providing an anchor value for the soil-water retention curve that corresponds to a water potential of pF at least 3.8; and characterize the soil sample based on the soil-water retention function. In some embodiments, the soil-water retention function is a Campbell soil-water retention function. In some embodiments, the anchor value corresponds to a water potential of pF at least 4.0. In some embodiments, the spectrophotometer is configured for vis-NIR spectroscopy analysis and the spectroscopy data is vis-NIR data. In some embodiments, the first model parameter is determined based on the spectroscopy data. In some embodiments, the first model parameter is empirically determined.

In another aspect of the current disclosure, further methods for characterizing soil at a sample site are provided. In some embodiments, the methods comprise: receiving into a spectrophotometer device, at the sample site, a soil sample from the sample site; analyzing the soil sample, with a spectrophotometer of the spectrophotometer device to provide spectroscopy data for the soil sample, and with one or more computing devices of the spectrophotometer device, based on the spectroscopy data and a soil model accessed by the spectrophotometer device, determining a first model parameter for a soil-water retention function anchored at pF at least 3.8 or at pF at least 4.2, thereby characterizing the soil sample based on the soil-water retention function, the soil model being determined based on spectroscopy data acquired from a plurality of other soil samples. In some embodiments, the model is the Campbell soil-water retention function. In some embodiments, the soil sample is not sieved, not ground, and not oven dried. In some embodiments, the soil sample is classified as one or more of loamy sand, sandy loam, loam, silt loam, silt, sandy clay loam, clay loam, silty clay loam, sandy clay, silty clay, or clay.

DETAILED DESCRIPTION

Figure 1:
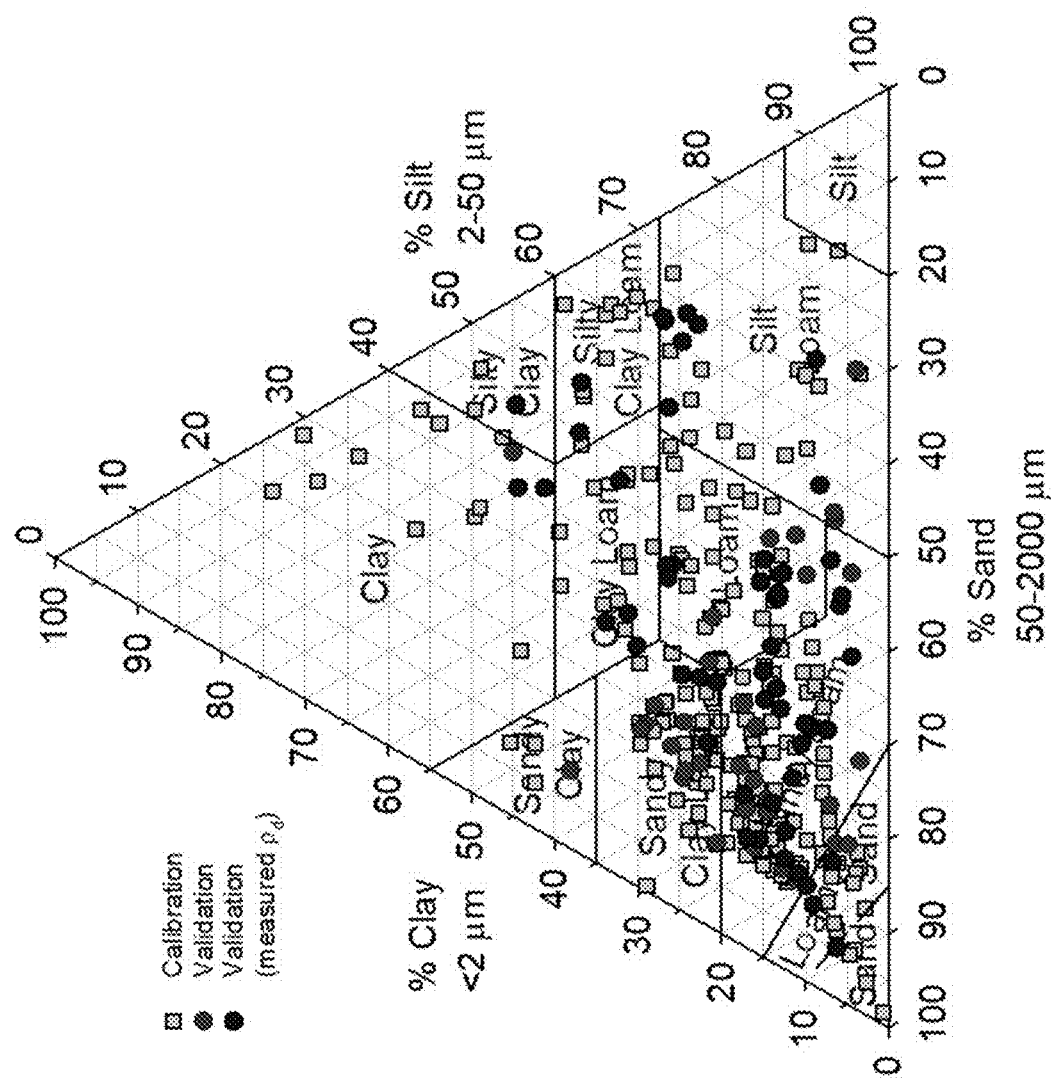
FIG. 1 shows a distribution of the soil samples in the USDA soil texture triangle for the calibration and validation datasets. The darker circles indicate samples for which the bulk density (pa) was measured, and this dataset was used for the comparison of visible-near infrared spectroscopy with a known computer program for estimating SWRCs (ROSETTA-1). The lighter circles indicate soil samples for which the pa was not measured.

As used herein, soil matric potential (ti) is the potential that is derived from the surface tension of water menisci between soil particles. The magnitude of matric potential depends on the soil water content, the size of the soil pores, the surface properties of the soil particles, and the surface tension of the soil water. In some cases, as is well known in the art, matric potential can be expressed by taking a common log of the matric potential, referred to as pF.

As used herein, soil-water retention curve (SWRC) is the relationship between soil/water matric potential and volumetric soil-water content at equilibrium above the reference (zero) level represented by the free water table at atmospheric pressure.

Reliable estimation of SWRC at a high spatial resolution is a prerequisite for accurate modeling and forecasting in different disciplines (e.g. hydrogeology, environmental geosciences), making vis-NIRS highly attractive alternatives to cost-, time- and labor-intensive direct measurements. Under some embodiments of the technology, vis-NIR methods and related systems can be used to rapidly and accurately estimate Campbell soil-water retention function. In some embodiments, a method disclosed herein can predict the Campbell soil-water retention function for all currently existing soil texture classes and with varying soil organic matter, including from topsoils to subsoils. In some embodiments, a method disclosed herein can only require brief scanning of the soil samples with a portable (or other) vis-NIR spectrometer to generate the estimated Campbell soil-water retention function. Consequently, in some cases, end-users may not need to have any expertise in soil and hydrological sciences to derive vital SWR information from raw soil samples. More broadly, embodiments of the disclosed method are generally more accurate, more cost-effective, and faster compared to conventional lab-based methods, which can take weeks to analyze the samples.

Some embodiments can employ a particular anchor point for determining a SWRC for a soil sample (e.g., pF of 3.8 or more) to provide particularly and unexpectedly accurate results. For example, the original Campbell function has a reference point at saturated water content $θ_s$ which is strongly related to soil structure and total porosity and less strongly related to texture. Thus, this reference point is poorly predicted from the vis-NIR spectroscopy. In contrast, in some embodiments disclosed herein, the Campbell function is instead anchored at a drier water content, pF 3.8-4.2 (e.g. ψ=−$10^{4.2}$, with log|−$10^{4.2}$|=pF 4.2), instead of $θ_s$. Spectral models can then be used to accurately predict the parameters of the anchored Campbell SWR function (Campbell b and water content at pF 3.8-4.2) for topsoils as well for subsoils covering all currently existing soil texture classes and with varying soil organic matter.

Figure 2:
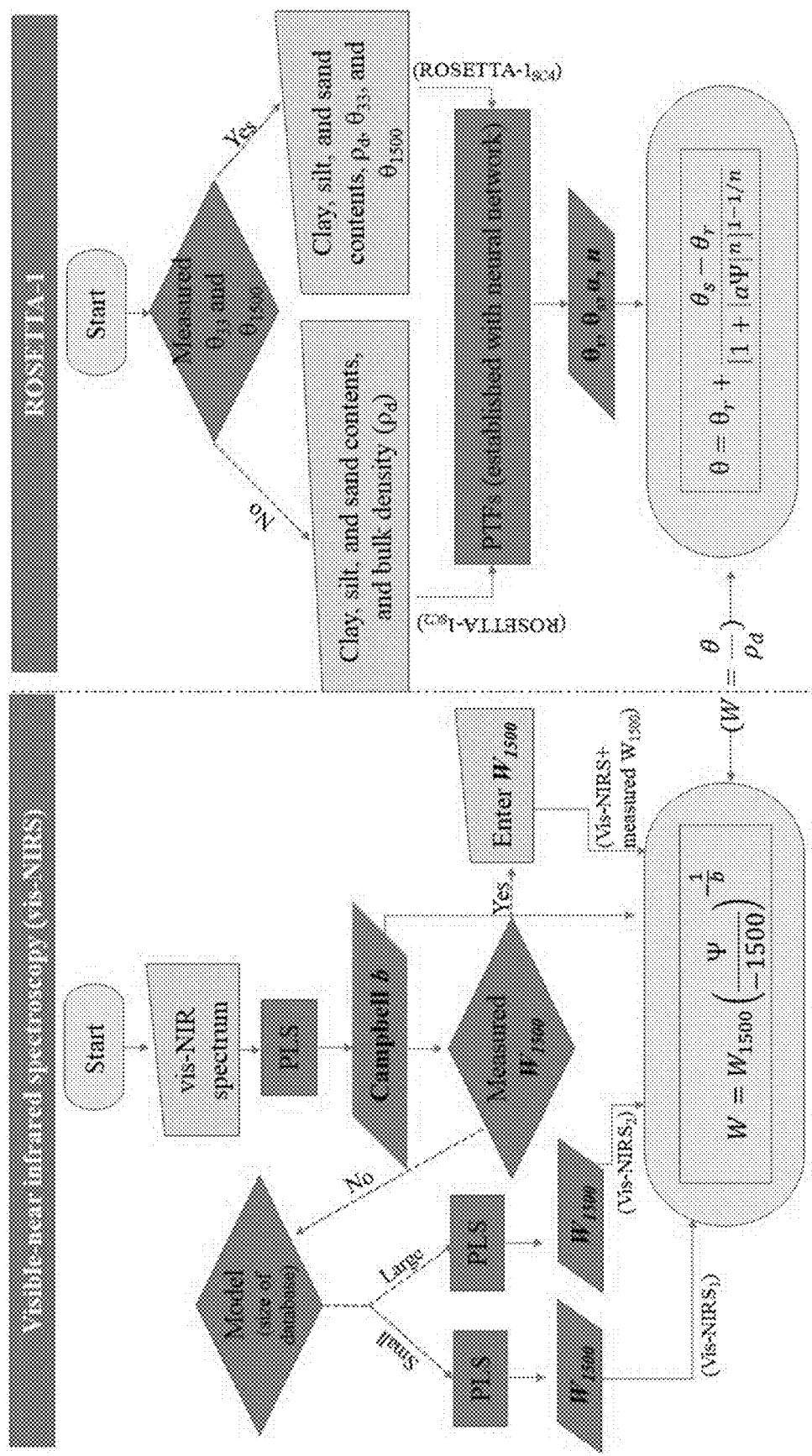
FIG. 2 shows a flowchart of two methods—visible-near infrared spectroscopy according to some embodiments, and ROSETTA-1—for estimating water contents (W: gravimetric water content, and θ: volumetric water content) at each soil-water matric potential (ψ). The Campbell b is the pore-size distribution and the $W_{1500}$ is the gravimetric water content at −1500 kPa. θr, θs, α, and n is the residual and saturated water contents, and the van Genuchten parameters, respectively.

Further in this regard, some embodiments of a method for estimating the soil-water retention curve for a soil sample can include measuring the vis-NIRS data from a soil sample. A model parameter for a soil-water retention function (e.g., the Campbell function) can then be determined, based on the spectroscopy data, and the soil sample can then be characterized based on the soil-water retention function. In particular, as also discussed above, a first model parameter can provide an anchor value for the soil-water retention curve, which in particular can be between a water potential of pF 3.84.2, inclusive (e.g. 3.80, 3.85, 3.90, 3.95, 4.00, 4.05, 4.10, 4.15, 4.20). An exponential shape parameter (b) can also then be determined based on the spectroscopy data, and these two model parameters can be used in conjunction with the aforementioned soil-water retention function to develop a soil-water retention curve for a soil sample. In some embodiments, the soil-water retention function used in the method is, for example, $$\Psi = -1500 \left(\frac{W}{W_{1500}}\right)^{-b},$$

wherein $W_{1500}$ is the gravimetric water content [kg kg$^{-1}$] at $-1500$ kPa, or pF 4.2. (In this regard, it is recognized that gravimetric water content (W) can be converted to volumetric water content ($\theta$) by multiplying W by soil bulk density ($\rho_4$), including as shown in FIG. 2 and further discussed relative to examples below.)

Some methods described herein include analysis with a spectrometer. In some embodiments the spectrometer analyses absorbance in the visible to near infrared range. In some embodiments the spectral range analysed by the spectrometer is 350-2500 nm.

Some methods described herein include steps to prepare soil samples for analysis with a spectrometer. In some embodiments, a soil sample is air-dried and sieved, as can support measurements that are more representative of microporosity than other approaches (e.g., untreated core samples). In some embodiments the sieve used has a pore diameter of <2 mm. In some embodiments, soil samples are derived from core samples.

Embodiments of the present invention are described herein using several definitions, as set forth above and throughout the disclosure. The disclosed subject matter may be further described using definitions and terminology as follows. The definitions and terminology used herein are for the purpose of describing particular embodiments only and are not intended to be limiting.

As used in this specification and the claims, the singular forms "a," "an," and "the" include plural forms unless the context clearly dictates otherwise. For example, the term "a substituent" should be interpreted to mean "one or more substituents," unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover, the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

EXAMPLES

The following Examples are illustrative and should not be interpreted to limit the scope of the claimed subject matter.

Example 1—Rapid Estimation of a Soil-Water Retention Curve Using Visible-Near Infrared Spectroscopy Estimation of a soil-water retention curve (SWRC) is essential for modeling the water flow and solute transport. A simple method to fit the measured soil-water retention data is the Campbell SWR function. In this example, the Campbell function with an anchored gravimetric water content at $-1500$ kPa ($W_{1500}$) was used, which included two unknown parameters, Campbell b (negative slope on a log scale of SWRC) and $W_{1500}$. An inexpensive methodology was proposed for predicting these Campbell parameters using visible-near infrared spectroscopy (vis-NIRS). Three calibration Partial Least Squares Regression models were developed. The first calibration model built on 230 soil samples predicted Campbell b and $W_{1500}$ (vis-NIRS$_1$). The second model used the same dataset for predicting Campbell b but included 1570 soil samples for predicting $W_{1500}$ (vis-$NIRS_2$). The third model combined predicted Campbell b from the 230 soil samples with measured $W_{1500}$ (vis-NIRS+measured $W_{1500}$), similar to approaches used in ROSETTA-1 software. The fourth model used the entire datasets without splitting them into calibration and validation (vis-$NIRS_3$). The $R^2$ of the Campbell b and $W_{1500}$ ranged from 0 to 0.89 and 0.02-0.91, respectively. Results showed that predicted SWRCs were comparable with estimates from the ROSETTA-1 for two scenarios: using soil texture and bulk density as inputs (ROSETTA-$1_{sc2}$) and using soil texture, bulk density, volumetric water content at −33 and −1500 kPa (ROSETTA-$1_{sc4}$). It was concluded that the vis-NIRS based models captured the shapes of the SWRC and vis-$NIRS_2$ and vis-NIRS+measured $W_{1500}$ could be used as an alternative to ROSETTA-$1_{sc2}$. Future research is needed to improve the performance of the vis-NIRS models by including more calibration soil samples, particularly for sandy soils.

By way of further introduction, and with further reference to the summary discussion above, modeling of soil variable saturated flow and contaminant transport requires knowledge of the soil hydraulic properties, such as the soil-water retention curve and hydraulic conductivity, soil water diffusivity, and climatic conditions and agricultural practices. The non-linear relation between soil water content and matric potential is considered a crucial hydraulic property in the vadose zone describing the amount of water retained in a porous medium at a given matric potential, and the relationship depends on soil-texture, pore geometry, and discontinuity (Sharma and Uehara, 1968; Williams et al., 1983). Furthermore, soil moisture characteristics are essential for describing the availability of soil water to plants and simultaneously, are fundamental input in water flow and solute transport modeling (Varvaris et al., 2020; Varvaris et al., 2019). Several models (mechanistic and empirical) have been proposed for accurately fitting the measured soil-water retention at the wet end or in drier conditions (Campbell and Shiozawa, 1992; Campbell, 1974; Or and Tuller, 1999; Oswin, 1946; Rossi and Nimmo, 1994; van den Berg and Bruin, 1981; van Genuchten, 1980).

Determination of SWRC through direct measurements under conventional approaches can be a laborious and time-consuming process. Furthermore, the spatial variability of the soil properties within a field may require a large number of soil samples to reduce uncertainties in relation to hydrogeological modeling, because SWRCs are essential for the modeling of water transport and biochemical processes in the unsaturated zone (Mader, 1963; Nielsen et al., 1973; Peck et al., 1977; Pham and Fredlund, 2008; Varvaris et al., 2018; Varvaris et al., 2019; Wood et al., 1988).

In some cases, to improve speed, expense and accuracy, a method that is well established and has successfully been used as an alternative for determining SWRC is the pedo-transfer function (PTF) (Iversen et al., 2011; Kotlar et al., 2019; Pittaki-Chrysodonta et al., 2019; Silva et al., 2017; Varvaris et al., 2021b). A PTF can be developed when knowledge of typically available soil properties such as clay content, organic matter, bulk density is available. Several researchers have developed PTFs for predicting the SWRC using typically known soil properties such as soil texture and bulk density (Clapp and Homberger, 1978; Gupta and Larson, 1979; Pittaki-Chrysodonta et al., 2018; Rudiyanto et al., 2021; Schaap et al., 1998). Schaap et al. (2001) developed a computer program, ROSETTA-1, for estimating SWRCs by implementing hierarchical PTFs. More recently, Rudiyanto et al. (2021) improved the PTFs using the neuro-m neural networks approach with different sets as inputs such as soil textural class or sand, silt, and clay contents, and bulk density.

Rosetta

In some cases, as generally discussed above, soil properties can be predicted using visible-near-infrared spectroscopy (vis-NIRS), which may be relatively simple, rapid (a measurement takes only a few seconds), reproducible, and non-destructiveness and generally avoids the use of hazardous chemicals (Pittaki-Chrysodonta et al., 2019; Stenberg et al., 2010). Moreover, vis-NIRS methods can require very little sample preparation (e.g., air-drying and sieving) before analysis, which can make this method more advantageous compared to other conventional laboratory methods.

However, despite the beneficial qualities of vis-NIRS, work ranging over decades has failed to reliably predict SWRCs across a wide range of soil classes and other conditions. Thus, there is a longstanding need to appropriately apply vis-NIRS for predicting the SWRC in a more practical, reliable, and comprehensive way.

In this regard, the objectives of the study presented in this example were to 1) develop vis-NIRS models for predicting the two parameters of the anchored Campbell soil water retention function for 11 soil textural classes, 2) evaluate the models' performance a) based on an independent validation dataset, b) within different textural classes, c) for horizon specific models (by predicting the vis-NIRS SWRC for subsoils using a calibration model derived from topsoil spectral data and vice versa), d) to improve the vis-NIRS models by adding one measurement −1500 kPa or predicted from a large vis-NIRS dataset and e) by comparing the vis-NIRS predicted SWRC with the predictions obtained from the ROSETTA PTFs across different soil textural classes and at different soil-water matric potentials.

A total of 306 (small library) and 1,658 (larger library) soil samples were included in this study which were obtained from the National Soil Survey Center (NSSC) Kellogg Soil Survey Laboratory (KSSL) database. The database contains soil pedons, with measured chemical and physical properties representing geographically diverse soils from across the conterminous United States, Hawaii, and Alaska (Seybold et al., 2019). The soil samples were collected from topsoil and subsoil.

In order to determine the soil texture distribution, the clay, silt, and sand contents were measured based on the pipette method (Kilmer and Alexander, 1949). The soil-water retention data were measured for seven matric potentials at: −6, −10, −33, −100, −200, −500, and −1500 kPa. The soil samples were air-dried, ground, and <2-mm sieved. The pressure-plate (3C1a-e1a) and pressure-membrane (3C2a1a-b) extraction methods were used to determine the water retention at from −6 up to −500 and at −1500 kPa, respectively. Briefly, an air-dried, sieved soil sample is placed in a retainer ring sitting on a porous ceramic plate in a pressure-plate extractor (for water contents at from −6 up to −500 kPa) or on a cellulose membrane in a pressure-membrane extractor (for water content at −1500 kPa). The plate and the membrane are covered with water to wet the samples by capillarity and the soil sample is equilibrated at the specified matric potentials. The pressure is kept constant until equilibrium is obtained according to known methods (Klute, 1986) and then the gravimetric water content is determined. Detailed information about the methods for the determination of the soil-water contents are according to Soil Survey Staff (2014).

As noted above, the Campbell soil-water retention function requires knowledge of a curve shape parameter, namely Campbell b, and the gravimetric saturated water content ($W_{gs}$) at the air-entry soil-water potential ($\Psi_e$). The Campbell (1974) soil-water retention function is given by:

$$\Psi = \Psi_e \left(\frac{W}{W_{gs}}\right)^{-b} \quad [1]$$

where $\Psi_e$ is the air-entry matric potential [kPa] and is the matric potential at which the air starts to enter to the largest pores in the soil. Campbell b is determined as the negative slope of the soil-water retention measurements on a log|–$\Psi$| vs log (W) system and can be considered as a pore-size distribution index (Moldrup et al., 2001). Moreover, it was found that the Campbell b, is strongly dependent on soil texture (Clapp and Hornberger, 1978; Pittaki-Chrysodonta et al., 2018).

For this example, Eq. [1] was modified relative to prior approaches to be anchored at −1500 kPa instead of $W_{gs}$, because the latter is mostly soil structure-dependent and less related to soil texture, whereas, for the former, vis-NIR data may more accurately represent actual soil texture.

Additionally, the estimation of $\Psi_e$ can vary substantially even within the same class and hence is not particularly texture-dependent. And at lower soil-water potentials, the soil-water contents are strongly related to the soil texture. Accordingly, with a modified anchor value, the updated Campbell soil-water retention function becomes:

$$\Psi = -1500 \left(\frac{W}{W_{1500}}\right)^{-b} \quad [2]$$

where $W_{1500}$ is the gravimetric water content [kg kg$^{-1}$] at −1500 kPa. Thereafter, calibration models for the two parameters of Campbell b and $W_{1500}$ need to be developed. For this study, only the soil samples that yielded an $R^2 > 0.9$ between the log|–$\Psi$| vs log (W) were included.

The spectrometer used was the ASD LabSpec 2500 (Analytical Spectral Devices, Inc., Boulder, CO) with a spectral range of 350-2500 nm with a spectral resolution of 3 nm and 10 nm at 700 nm and 1400 nm, respectively. The spectral interval is 1 nm. The air-dried soil samples were initially ground, and sieved to <2-mm, then loaded into a sample holder (pucks) and pressed to 46 psi, to assure that there is no void space. The sample holder is placed onto a Muglight lamp and scanned iteratively three times. In order to calibrate the spectrometer, a white reference panel was used prior to scans and after every ca. 30 min (McDowell et al., 2012). Spectral measurements were transformed from reflectance into apparent absorbance by log(reflectance$^{-1}$).

To improve the quality of the spectral data, different pre-processing techniques were applied. These techniques reduce undesired scatter effects such as baseline shifts and non-linearities (Rinnan et al., 2009; Wetterlind et al., 2013). The tested pre-processing techniques for this study were the Savitzky-Golay and Gap-Segment derivatives (Norris, 2001; Savitzky and Golay, 1964), standard normal variate (SNV) transformation and detrending (Barnes et al., 1989) and the orthogonal signal correction (OSC) (Sjöblom et al., 1998). With the derivatives, additive and multiplicative effects could be removed by taking the derivative of the spectral responses with respect to wavelengths. In order to estimate the first derivative, the difference between two successive spectral measurement points is calculated. For the second derivative, the difference between two successive points of the first-order derivative spectra is calculated. The SNV is a weighted normalization and calculates the standard deviation ($\sigma$) of the entire spectrum for the given sample and thereafter, the entire sample is normalized by this value (Barnes et al., 1989). Detrending fits a polynomial of a given order to the spectral data and subtracts this polynomial. The OSC removes the variance which is orthogonal to the reference value (Sjöblom et al., 1998). Finally, the spectral data were mean-centered, i.e., the mean offset from each variable was removed.

For the independent validation, the dataset of the 306 soil samples were divided into calibration (70%) and validation (30%) datasets. Cross-validation for all developed vis-NIRS models was performed using the leave-one-out cross-validation method. The cross-validation was performed using: (i) the calibration dataset and (ii) the entire dataset. The split was based on two criteria: 1) for each dataset, at least one sample derived from a textural class was included, and 2) The samples from each pedon were kept in the same dataset (calibration or validation). For validating horizon specific models, in the calibration dataset the topsoils or subsoils from the small library were included and respectively in the validation the subsoils or topsoils. For developing a second calibration model of the $W_{1500}$, a representative number of soils from a larger library were included samples (215 from the small library and 1352 from a larger database=1567).

In order to develop the calibration models, the partial least squares (PLS) regression analysis with the straight forward implementation of a statistically inspired modification of the PLS (SIMPLS) algorithm (de Jong, 1993) was used. In brief, this algorithm directly calculates the factors of the PLS as linear combinations of the original variables by maximizing a covariance criterion.

The carefully selection of the number of factors is important since the amount of variation in the spectral data should be maximized. However, higher or lower number of PLS factors would lead to an overestimation or underestimation, respectively. This number is defined as the local minimum value of the root mean square errors of calibration (RMSE$_{Cal}$) and cross-validation (RMSE$_{CV}$) that represented the most significant change in slope (Gowen et al., 2011).

The development of the PLS models was performed using the PLS Toolbox 8.8 software (Eigenvector Research) which is an advanced chemometric multivariate analysis tool within the MATLAB computational environment.

The ROSETTA-1 is a computer program based on neural network analyses with the bootstrap method which implements a number of pedotransfer functions (PTFs) for estimating van Genuchten water retention parameters and the saturated hydraulic conductivity (Schaap et al., 2001). The van Genuchten soil-water retention curve is given by:

$$\theta = \theta_r + \frac{\theta_s - \theta_r}{[1 + |\alpha\psi|^n]^{1-1/n}} \quad [3]$$

where $\theta r$ and $\theta_s$ [cm$^3$ cm$^{-3}$] denote the residual and saturated volumetric water contents, respectively, $\alpha$ [cm$^{-1}$] is related to the inverse of the air entry pressure, and n is a measure of the pore-size distribution index (van Genuchten, 1980).

For estimating the parameters of the van Genuchten, ROSETTA-1 includes five hierarchical models depending on the input data:

H1) The first hierarchical model is a class PTF that provides parameter averages for each USDA textural class.

H2) It uses as inputs the sand, silt, and clay contents (SSC).

H3) In addition, it includes bulk density (SSCBD).

H4) In addition, it uses a volumetric water content at −33 kPa (SSCBDθ$_{33}$).

H5) In addition, it includes a volumetric water content at −1500 kPa (SSCBDθ$_{33}$θ$_{1500}$).

In this study, the vis-NIRS predicted SWRC of the independent validation were compared with H3 and H5. The H3 and H5 were namely scenario 2 (ROSETTA-1$_{sc2}$) and scenario 4 (ROSETTA-1$_{sc4}$).

The developed PLS models of the two parameters (W$_{1500}$, Campbell b) were evaluated using the square of the Pearson correlation coefficient R (R$^2$), bias, and RMSE.

R$^2$, bias, and RMSE are defined as:

$$R^2 = \frac{\left[N\sum_{i=1}^{N}(y_i - \overline{y})(\widehat{y_{p,i}} - \overline{\widehat{y_p}})\right]^2}{\sum_{i=1}^{N}(y_i - \overline{y})^2 \sum_{i=1}^{N}(\widehat{y_{p,i}} - \overline{\widehat{y_p}})^2} \quad [4]$$

$$\text{Bias} = \overline{\widehat{y_p}} - \overline{y} \quad [5]$$

$$RMSE = \sqrt{\frac{1}{N}\sum_{i=1}^{N}(y_i - \widehat{y_{p,i}})^2} \quad [6]$$

where N is the number of samples, $y_i$ is the measurements, $\widehat{y_{p,i}}$ the predicted values, $\overline{y}$ the mean value of the measurements, an $\overline{\widehat{y_p}}$ is the average of the predicted values. In order to examine whether the vis-NIRS models were over-fitted, in addition to the cross-validation and validation, a permutation test (n=50) was further conducted. In brief, permutation tests repeatedly and randomly reorder the soil property (Y) by rebuilding the calibration model with its current settings after each reordering. Specifically, the evaluation was based on the pairwise Wilcoxon signed-rank, pairwise signed-rank, randomization t-tests, and plots of sum squared (SSQ) Y versus Y-block correlation. The permutation tests were performed for the models that were developed using the entire dataset (306 and 1658 soil samples included in Campbell b and W$_{1500}$, respectively).

To assess the performance of the vis-NIRS built on small (vis-NIRS$_1$) or larger library (vis-NIRS$_2$), vis-NIRS and a measured W$_{1500}$ (vis-NIRS+W$_{1500}$), and ROSETTA-1 predicted SWRC, the R$^2$, and RMSE of validation dataset, and the prediction bias were used. Specifically, the vis-NIRS predicted parameters (W$_{1500}$, Campbell b) for the three scenarios (vis-NIRS$_1$, vis-NIRS$_2$, vis-NIRS+W$_{1500}$) were inserted into the anchored Campbell function and the SWRC was obtained for each soil sample. For the ROSETTA-1, for each of two scenarios (ROSETTA-1$_{sc2}$, ROSETTA-1$_{sc4}$) the SWRC was obtained based on the van Genuchten equation using the predicted parameters from ROSETTA-1. The assessment was based on the water contents of the seven matric potentials (−6, −10, −33, −100, −200, −500, and −1500 kPa) for each soil sample. From the validation dataset, only the soil samples with measured bulk density (N=56) were included since the ROSETTA-1 predicted water contents are not gravimetric but volumetric. Therefore, the predicted volumetric water contents were converted into gravimetric. A flowchart of the two applied methods for obtaining an SWRC is illustrated in FIG. 2.

Figure 1A:
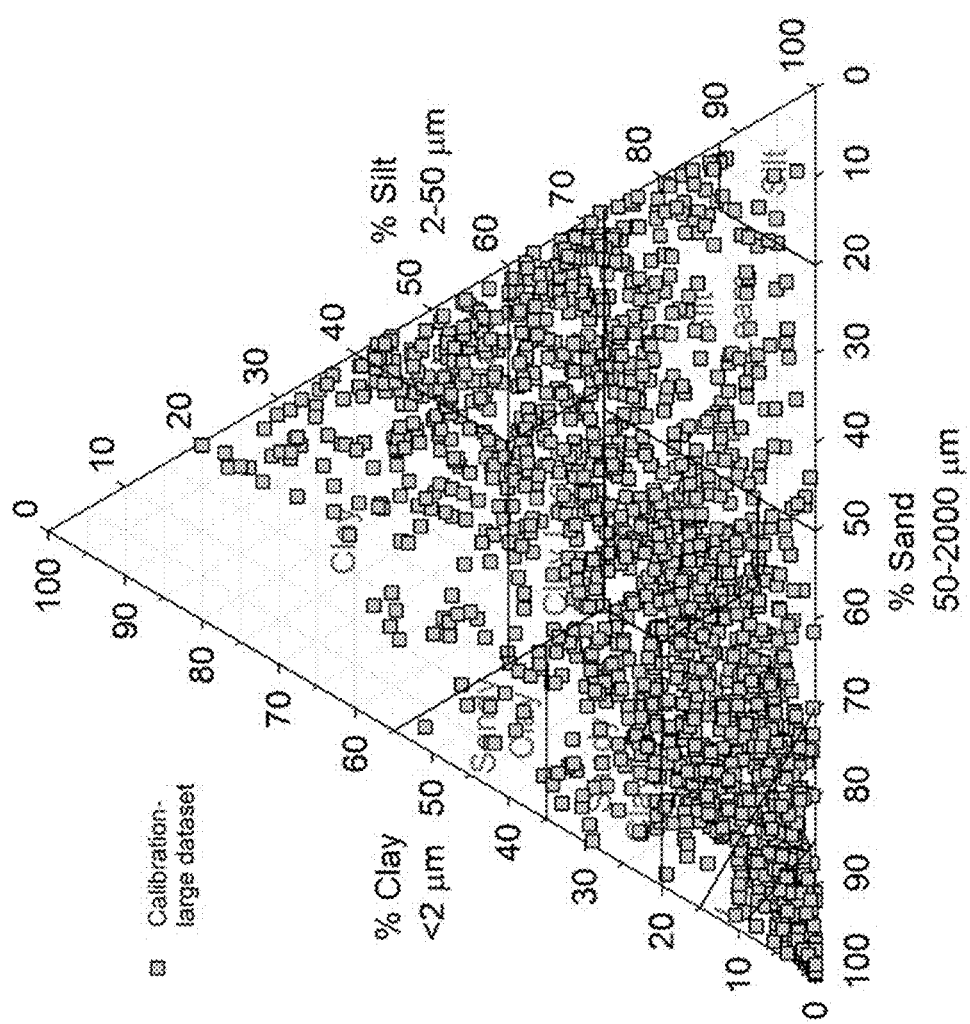
FIG. 1A shows a distribution of the soil samples in the USDA soil texture triangle for the calibration-large dataset used for developing a vis-NIR model of gravimetric water content at −1500 kPa.

The soil samples used for the development as well as for the validation of the PLS models covered 11 out of 12 USDA soil texture classes as shown in FIG. 1. The soil samples included in the larger library covered all the soil texture classes (FIG. 1A). In Table 1 (below), the mean, median, Q1, Q3, standard deviation (a), the skewness (skew), and the range (minimum-maximum) of W$_{1500}$ and Campbell b for each textural class for each dataset are presented.

The W$_{1500}$ ranged from 0.013 to 0.362, 0.001 to 0.598, and 0.018 to 0.229 [kg kg$^{-1}$] for the calibration of the small, larger, and validation datasets, respectively. The lowest mean values of W$_{1500}$ are presented in the textural classes with high percentage of sand such as sand (0.023, 0.025, and 0.026 kg kg$^{-1}$ for calibration of small and large, and validation datasets, respectively) and loamy sand (0.031, 0.050, and 0.032 kg kg$^{-1}$ for calibration of a small and large library, and validation, respectively), while the highest mean values are observed in the silty clay (0.260, 0.210, and 0.155 kg kg$^{-1}$ for calibration of a small and large library and validation, respectively) and clay (0.284, 0.228, and 0.183 kg kg$^{-1}$, for calibration of a small and large library and validation, respectively) classes. The median values are similar to the mean values for most of the classes for the calibration dataset of the smaller library, except of the loam (mean value equals to 0.096 and median 0.087 kg kg$^{-1}$) and silt loam (mean value equals to 0.124 and median 0.097 kg kg$^{-1}$). For the larger library, the median values were always lower than the average except for the silt class (mean value 0.047 and median 0.54 kg kg$^{-1}$). For the validation dataset, the median values are differentiated from the mean values for the loam (0.115 and 0.103 kg kg$^{-1}$ the mean and median, respectively) and clay (0.183 and 0.161 kg kg$^{-1}$ the mean and median, respectively) classes. However, the number of soil samples included in the clay textural class of the validation dataset is small (N=3). The highest a values are observed in silty loam (0.065 kg kg$^{-1}$) and silty clay (0.144 kg kg$^{-1}$) for the calibration dataset of the smaller library and in silty clay (0.076 kg kg$^{-1}$) and clay (0.068 kg kg$^{-1}$) for the calibration of the larger library. Silt loam (0.044 kg kg$^{-1}$), clay loam (0.043), and clay (0.040) have the highest values of the σ compared to other textural classes for the validation dataset. Regarding the skewness, for the calibration of the small library, only the silty clay loam (−0.298) and clay (−0.167) classes are left skewed while negative skewness for the validation dataset are presented in loamy sand (−0.467), sandy loam (−0.617), sandy clay loam (−0.407), and silty clay loam (−1.152). The dataset of the larger library presented only positive skewness. For the validation dataset for the sand, sandy clay and silty clay only the mean and median are estimated since the soil samples for each of these classes are less than three.

The values of the Campbell b were derived from the small library and the validation dataset and are varied from 2.41 to 8.41 and 2.08 to 7.19 for the calibration and validation dataset, respectively. The lowest value of Campbell b is observed in the loamy sand and sandy loam classes for the calibration and validation dataset, respectively. The highest value is presented in a sandy loam and in a silty clay soil for the calibration and validation dataset, respectively. The higher mean values of each class are observed in the classes with high percentage of sand or clay, while the loamier classes present lower values. The highest a is observed in sand (1.71) and loam (1.27) for the calibration and validation dataset, respectively. The lowest negative value of skew is observed in sandy clay loam (−1.31) and silty clay loam (−1.71) for calibration and validation dataset, respectively.

Figure 3:
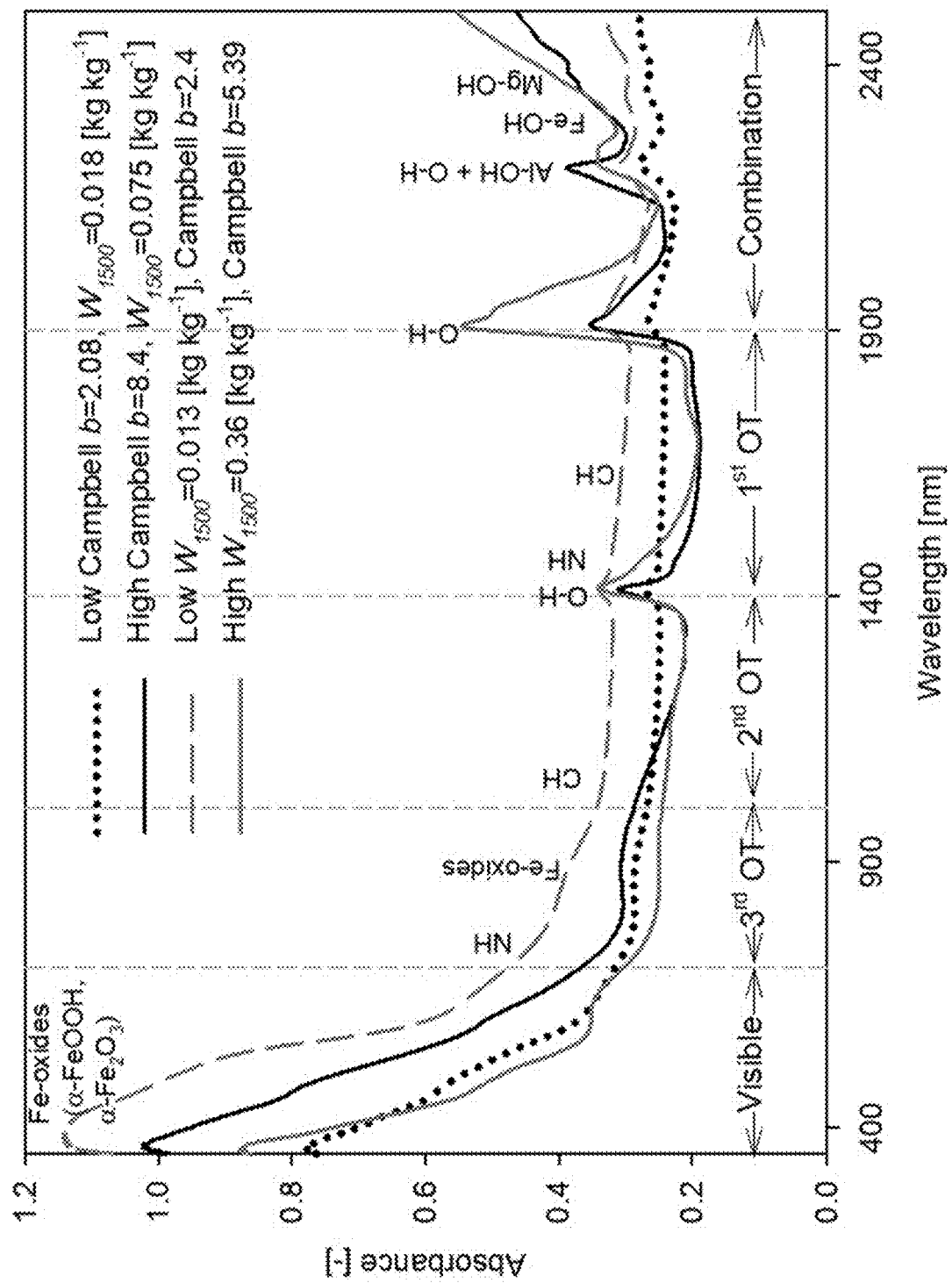
FIG. 3 shows spectral measurements for four soil samples: with low and high values of Campbell b (black lines), and with low and high values of gravimetric water content at −1500 kPa (grey lines). Solid and dashed/dotted lines indicate the high and low values, respectively, for each Campbell b. Also illustrated are the specific absorption bands of soil at different wavelengths. The vertical grey dashed lines denote the range in nm of the combination of first, second, and third overtone (OT) vibrations as well as the visible range.

In the FIG. 3, four absorption spectra of two soil samples with the lowest and highest values of Campbell b (2.08 and 8.4, respectively), and two with the lowest and highest values of W$_{1500}$ (0.013 and 0.36 kg kg$^{-1}$, respectively) are illustrated. It is observed that the samples with high values of Campbell b and $W_{1500}$ have stronger peaks compared to soils with low values near of 1400 and 1900 nm, while the sample with the highest value of Campbell b presents as well near of 2220 nm.

Figure 3A:
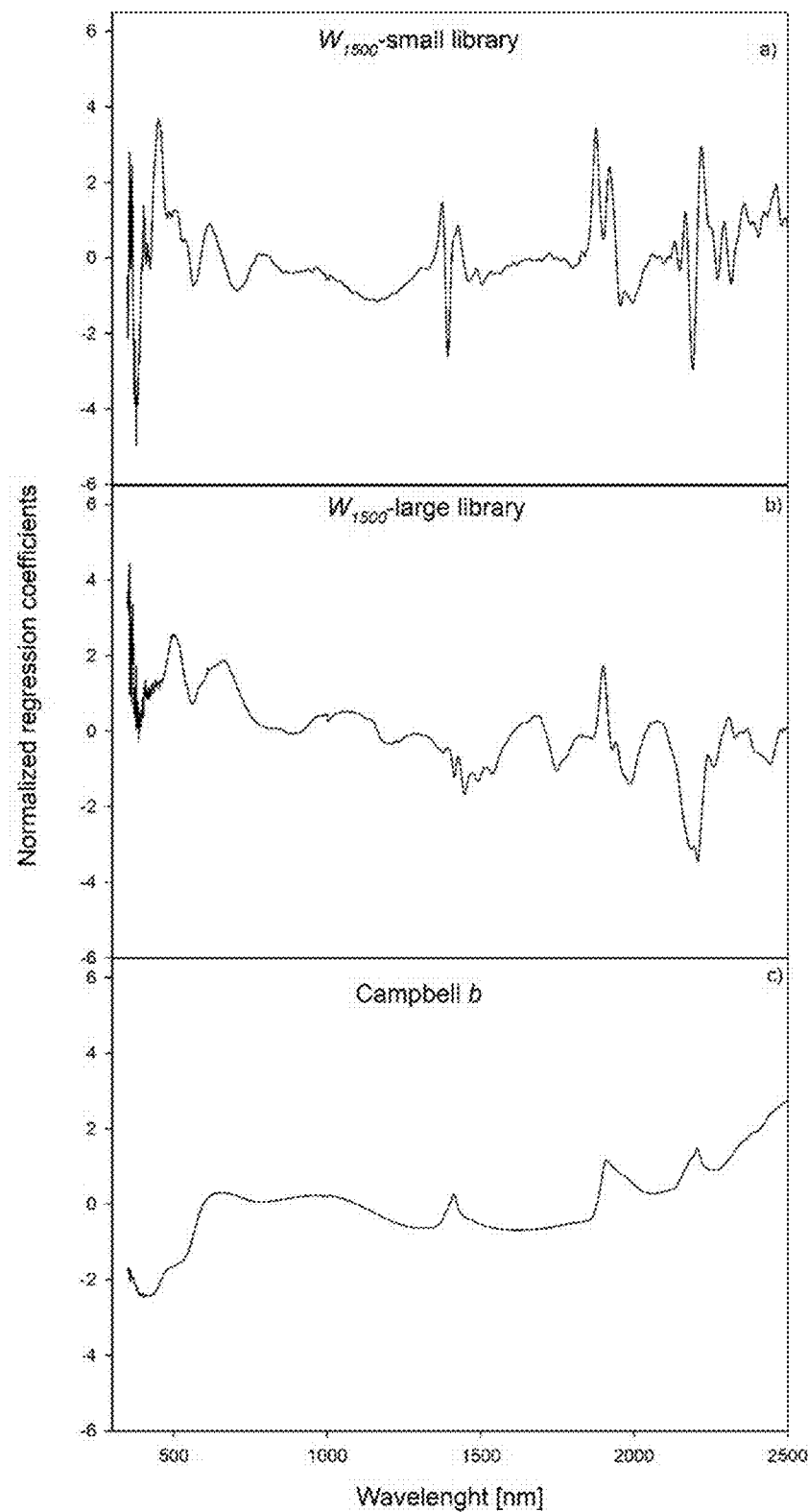
FIG. 3A shows normalized regression coefficients for Partial Least Squares calibration models of: a) gravimetric water content at −1500 kPa ($W_{1500}$) using the small library and b) the large library, based on first derivative, first order 6 factors, and c) pore-size distribution index (Campbell b) based on orthogonal signal correction and 2 factors.

The pre-processing techniques that yield the best PLS models were the Savitzky-Golay first derivative and OSC for the $W_{1500}$ and Campbell b calibration model of the small library, respectively, and OSC for the $W_{1500}$ of the larger library. The optimum number of factors were set to five and two for the $W_{1500}$ (for both models) and Campbell b. FIG. 3A illustrates the normalized regression coefficients as a function of wavelength for the three calibration models. The results of the three calibration models are presented in Table 2 (below). Specifically, the statistical characteristics of the cross-validation and validation dataset for each textural class are given. For the classes with less than five soil samples, the statistics were not calculated individually but were included to estimate the statistics for all soil samples.

Regarding the cross-validation dataset (Table 2A), the $R^2$, bias, and RMSE were 0.64, 0, 0.039, respectively for the $W_{1500}$ model of the small library and 0.52, 0, and 0.058 for the larger library, while for the Campbell b model, the respective figures were 0.56, 0, and 0.769. Based on the $R^2$ of the $W_{1500}$ model of the small library for each class, it is observed that the loamy sand, sandy loam, and sandy clay loam present values of $R^2$ close to 0. The sandy clay loam presented the highest RMSE value (0.073 kg kg$^{-1}$). The values of the $R^2$ and RMSE for the $W_{1500}$ of the larger library varied respectively from 0.15 (silty clay) to 0.64 (silt) and 0.039 (sandy clay loam) to 0.086 (silty clay) kg kg$^{-1}$. It is observed a higher RMSE of 0.086 kg kg$^{-1}$ in soil samples that their textural classes were not defined since the textural data were not available. The highest value of bias (0.046) was observed in the sand class. Low values of $R^2$ (ca. 0) of Campbell b model were presented in silt loam, clay loam, and clay classes but a high RMSE value (1.43) was observed in sandy clay loam.

For the validation dataset (Table 3), the statistics were worst compared to the cross-validation dataset for the small library. Specifically, for the predictions of the $W_{1500}$ the value of $R^2$, bias, and RMSE, were 0.34, 0.027, and 0.049 respectively, while for the predictions of the Campbell b figures were 0.19, 0.306, and 1.009, respectively. The silt loam class presented the lowest RMSE (0.031 kg kg$^{-1}$), of the $W_{1500}$ compared to the other classes, while the highest $R^2$ was observed in the loamy sand. The silt loam was presented the highest value of the $R^2$ (0.73) and the second-lowest value of RMSE (0.566) for the prediction of the Campbell b. The lowest RMSE was presented in the sandy clay loam class (0.501). Regarding the statistics obtained from the $W_{1500}$ of the large library, the loamy sand, sandy loam, and sandy clay loam presented lower RMSE compared to the statistics derived from the smaller library. The silt loam presented a slightly higher value of RMSE (0.036 instead of 0.031 kg kg$^{-1}$) and the loam has the same RMSE value (0.039 kg kg$^{-1}$) compared to the $W_{1500}$ of the smaller library. The absolute values of bias were lower for the $W_{1500}$ of the larger library among the five textural classes except for the silt loam. The $R^2$, bias, and RMSE for all samples included in the validation dataset were improved (0.49, 0.008 kg kg$^{-1}$, and 0.035 kg kg$^{-1}$, respectively instead of 0.34, 0.027 kg kg$^{-1}$, and 0.049 kg kg$^{-1}$, respectively) for the predicted from the larger library of the $W_{1500}$. The statistics of the sandy clay, clay loam, silty clay loam, silty clay, and clay were not available since the included soil samples into these classes were less than five soil samples.

The statistics obtained from the cross-validation using the entire datasets (small-for Campbell b and large-for $W_{1500}$) are presented in Table 2.C. It is observed that the values of $R^2$, Bias, and RMSE were similar to those obtained from the cross-validation of the calibration dataset (Table 2.A). Regarding the statistics obtained from the cross-validation of the Campbell b were slightly worst compared to these of Table 2.A. The permutation results yielded values of less than 0.05 for cross-validation for all tests (Wilcoxon, Sign test, and Rand t-test) for both models (Campbell b, and $W_{1500}$) and thus, the models were significant at the 95% confidence level. Additionally, based on FIG. S3, it is observed that the values of standardized sum squared of Y values from calibration and cross-validation were relatively close to each other and significantly lower than the un-permuted soil property (far right side of the plot) for both models (Campbell b, and $W_{1500}$). Therefore, the calibration models were significant and not over-fit.

Table 3 (below) presents the statistical characteristic of the predicted $W_{1500}$ and Campbell b derived from the topsoils (Table 3A) and subsoils (Table 3B) for each soil textural class when the calibration models were included only subsoils and topsoils, respectively for the smaller library. For the topsoil predicted $W_{1500}$ the $R^2$, bias, and RMSE were 0.49, 0.016 kg kg$^{-1}$, and 0.042 kg kg$^{-1}$, respectively, while for the Campbell b these figures were 0.55, 0.390, and 0.791, respectively. For the subsoils predicted $W_{1500}$ and Campbell b, $R^2$, bias, and RMSE, were respectively 0.05, −0.007 kg kg$^{-1}$, and 0.073 kg kg$^{-1}$ and 0.37, −0.226, and 1.075.

Figure 4:
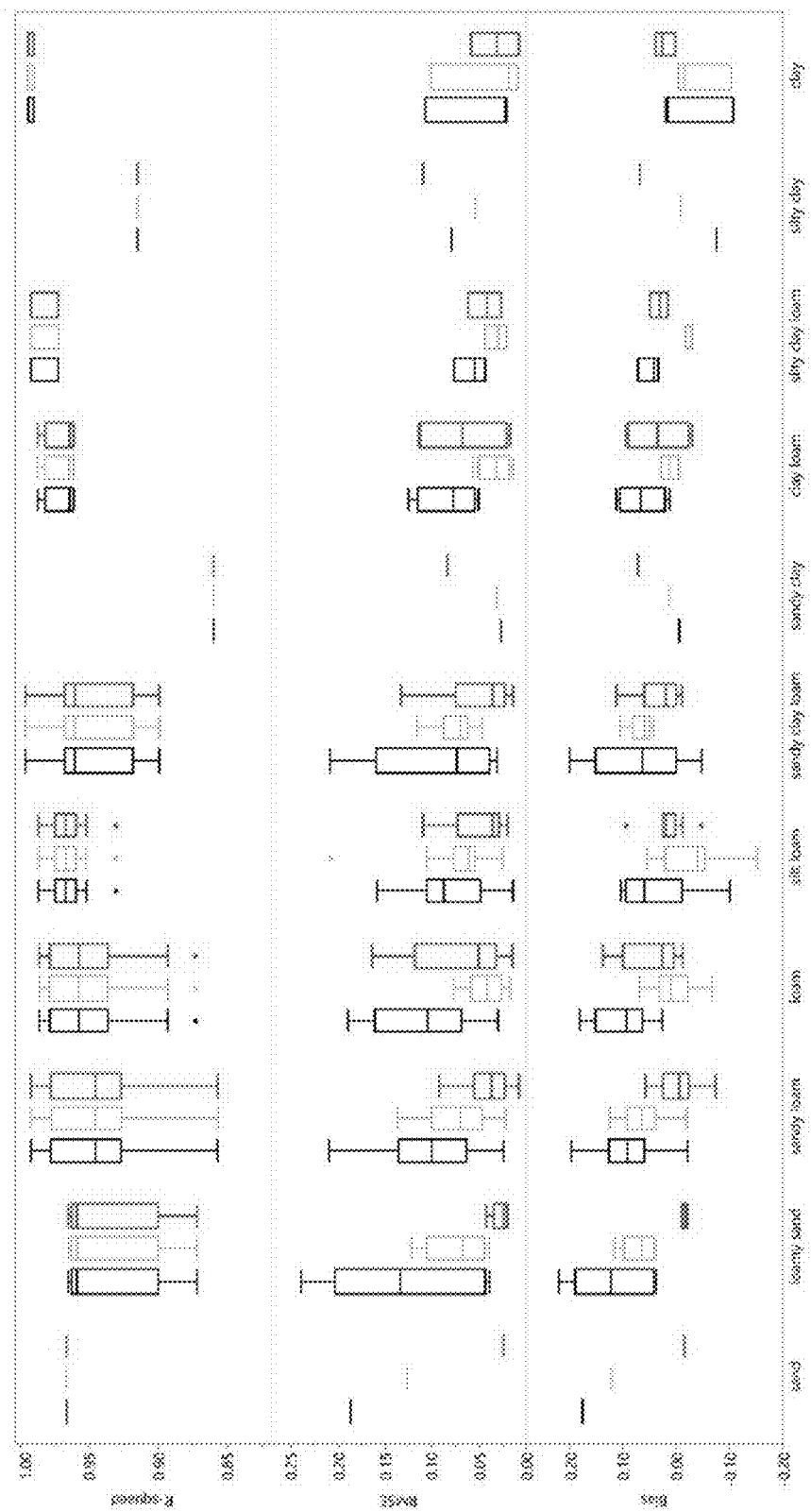
FIG. 4 shows box-and-whisker plots of R-squared, Root mean square error-RMSE, and Bias for each of multiple textural classes using a smaller (black) and a larger (light grey) library for predicting the gravimetric water content at −1500 ($W_{1500}$), and the measured (dark grey) $W_{1500}$. The statistics are based on vis-NIRS predicted soil-water retention and the measured points for the validation dataset. The predicted Campbell b is derived from the same dataset and thus, the box-and-whisker plots of $R^2$ are the same.

Except for the statistics of the three calibration models (vis-NIRS$_1$, vis-NIRS$_2$, vis-NIRS+measured $W_{1500}$) for the validation dataset, the $R^2$, RMSE, and bias, for each SWRC based on the vis-NIRS predicted soil-water retention and the measured points for the validation dataset were calculated. The results of these are shown in the box-and-whisker plots for each textural class in FIG. 4. All textural classes presented a high value of $R^2$ (ca. $R^2$>0.85) between the measured and predicted gravimetric water contents at the seven matric potentials of each sample. Moreover, it is observed that the $R^2$ is the same for the three vis-NIRS scenarios since the values of the Campbell b were predicted using the same calibration model obtained from the small library. Regarding the predictions obtained from the small library (vis-NIRS$_1$), the values of the RMSE varied from 0.014 to 0.239, and a mean value of 0.097 kg kg$^{-1}$ with the lowest and highest values to be observed in silt loam and loamy sand class, respectively. The values of bias were from −0.10 to 0.22, with the silty clay loam and loam classes to be least and most biased, respectively. Lower values of the RMSE were observed in the predictions obtained from the larger library (vis-NIRS$_2$). Specifically, the RMSE ranged from 0.009 (clay) to 0.207 (silt loam) with an average of 0.065 kg kg$^{-1}$. The bias for the predictions obtained from the larger library varied from −0.15 to 0.12 with an average of 0.03 kg kg$^{-1}$. When a measured point at −1500 kPa was included, the RMSE values were improved (0.008-clay to 0.164-loam, with an average of 0.049) and the bias ranged from −0.073 to 0.138 with a mean value of 0.018 kg kg$^{-1}$. Based on FIG. 4, it was observed that the RMSE values when the predictions were derived from the calibration model of the larger library were significantly improved for all textural classes.

Figure 5:
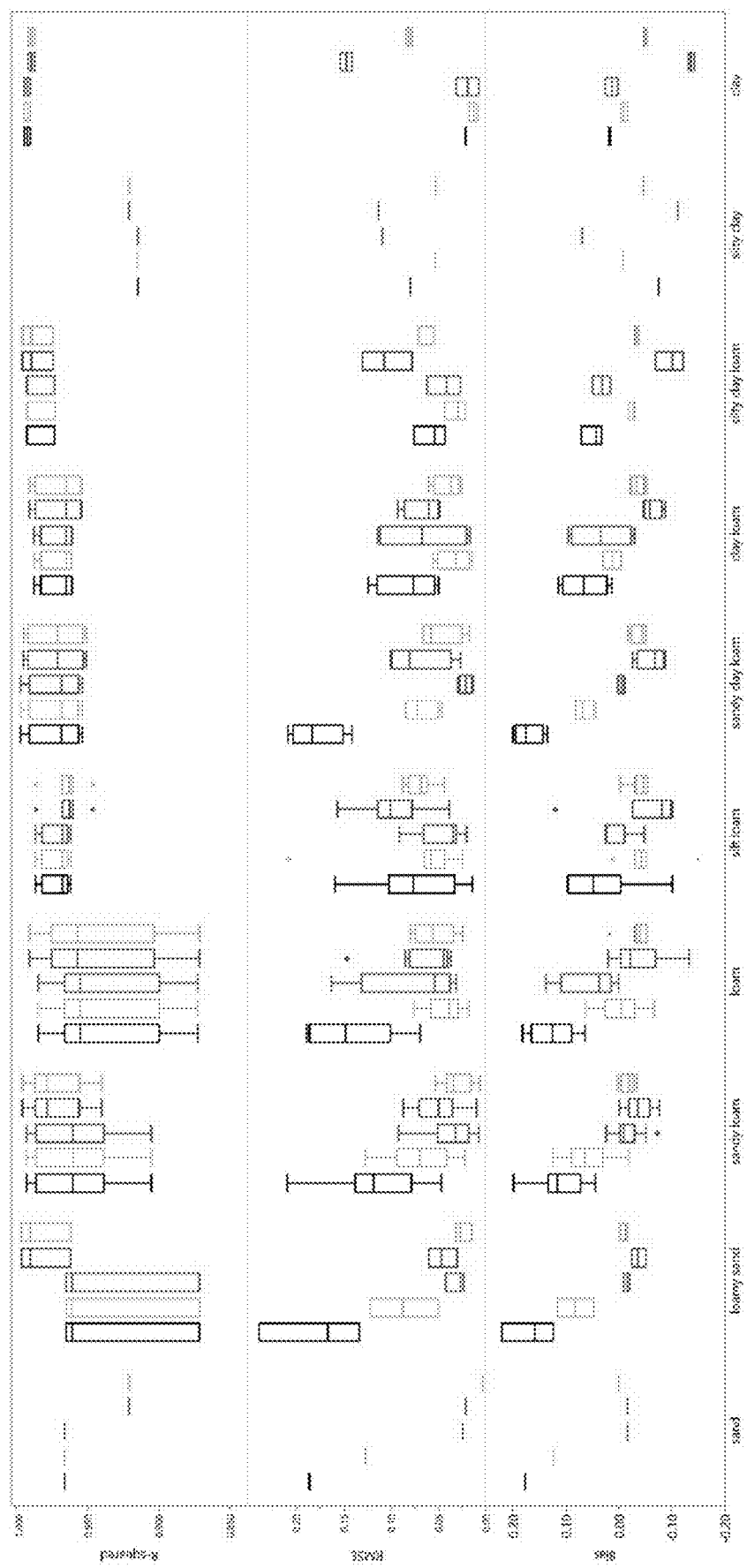
FIG. 5 shows box-and-whisker plots of R-squared, Root mean square error-RMSE, and Bias for each of multiple textural class for five scenarios (ordered from left to right for each class): visible-near infrared spectroscopy (vis-NIRS) based on a small dataset and a larger library, vis-NIRS, and measured gravimetric water content at −1500, ROSETTA-$1_{sc2}$, and ROSETTA-$1_{sc4}$ predicted soil-water retention curve. The statistics are based on the predicted and the measured points for the validation dataset for each scenario.

In FIG. 5 the box-and-whisker plots of the three statistics ($R^2$, RMSE, and Bias) for each textural class for the five scenarios (three for vis-NIRS and two for ROSETTA-1) are illustrated. The scenarios were the vis-NIRS$_1$, vis-NIRS$_2$, vis-NIRS+measured $W_{1500}$, ROSETTA-1$_{sc2}$, and ROSETTA-14 predicted soil-water retention curve. It was observed that except for the loamy sand class, the vis-NIRS predicted SWRC yielded higher values of $R^2$ compared to ROSETTA-$1_{sc2}$. The values of the $R^2$ for the ROSETTA-$1_{sc4}$ were lower compared to ROSETTA-$1_{sc2}$ for all textural classes except for sand. The silty clay loam (0.65-0.9) and clay (0.53-0.64) classes presented the lowest values of $R^2$. The values of the RMSE for the vis-NIRS$_1$ predicted SWRC for all classes were higher compared to the other four scenarios except for the silt loam, in which the higher values of RMSE were presented in ROSETTA-$1_{sc2}$. The lowest values of RMSE were observed in the vis-NIRS+measured $W_{1500}$ and vis-NIRS$_2$ scenarios except for the sand class, in which the ROSETTA-$1_{sc4}$ presented the lowest values of RMSE. By observing the values of the bias, the predictions obtained from the ROSETTA-$1_{sc4}$ were least biased compared to ROSETTA-$1_{sc2}$, while the most biased predictions were obtained from vis-NIRS$_1$.

FIG. 5 represents the values of the RMSE and bias obtained from the five scenarios at seven soil-water matric potentials (−6, −10, −33, −100, −200, −500, and −1500 kPa). It is observed that the vis-NIRS$_1$ presented the highest values of RMSE and bias. The wettest point (−6 kPa) was better predicted (RMSE=0.096 kg kg$^{-1}$) from the vis-NIRS$_2$, while close values of the RMSE were observed in vis-NIRS+measured $W_{1500}$ (0.102 kg kg$^{-1}$) and ROSETTA-$1_{sc4}$ (0.103 kg kg$^{-1}$). For the RMSE of the soil-water matric potentials at −10, −33, −100, and −200 the ROSETTA-$1_{sc4}$ presented the lowest values (0.059, 0.016, 0.023, and 0.023 kg kg$^{-1}$) compared to the other four scenarios. For the driest soil-water matric potentials (−500, and −1500 kPa), the vis-NIRS+measured $W_{1500}$ presented lower RMSE values, while the vis-NIRS$_2$, ROSETTA-$1_{sc2}$, and ROSETTA-$1_{sc4}$ illustrated similar values. The least biased predictions were observed in vis-NIRS+measured $W_{1500}$ and vis-NIRS$_2$.

Figure 6:
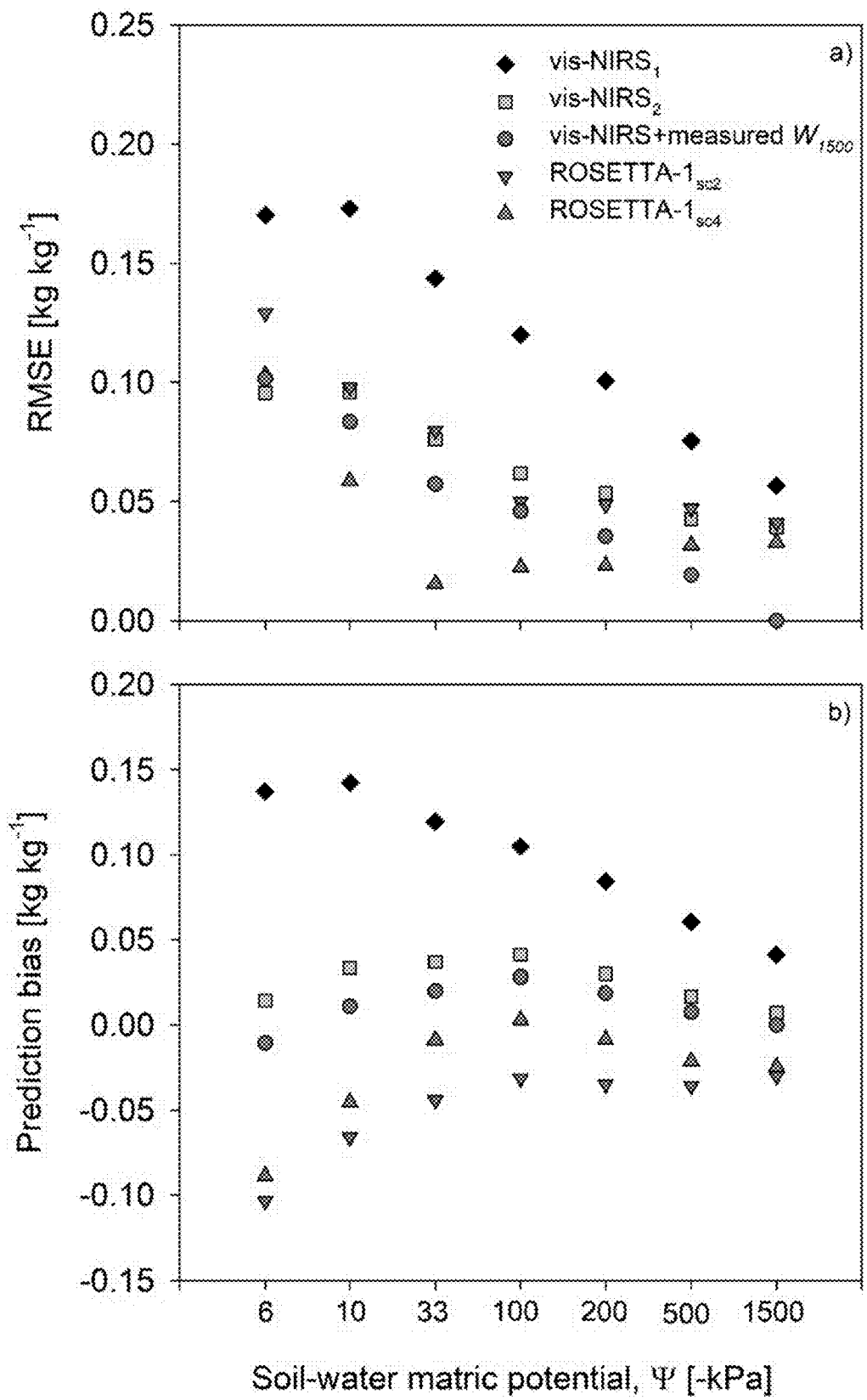
FIG. 6 shows: a) Root mean square error (RMSE) and b) prediction bias for seven soil-water matric potentials for 56 soil samples estimated with visible-near infrared spectroscopy (vis-NIRS) built on a small (vis-NIRS$_1$) and a larger (vis-NIRS$_2$) library, vis-NIRS and a measured gravimetric water content at −1500 kPa (vis-NIRS+measured $W_{1500}$), ROSETTA-1 scenario 2 (ROSETTA-$1_{sc2}$) and scenario 4 (ROSETTA-$1_{sc4}$).
Figure 7:
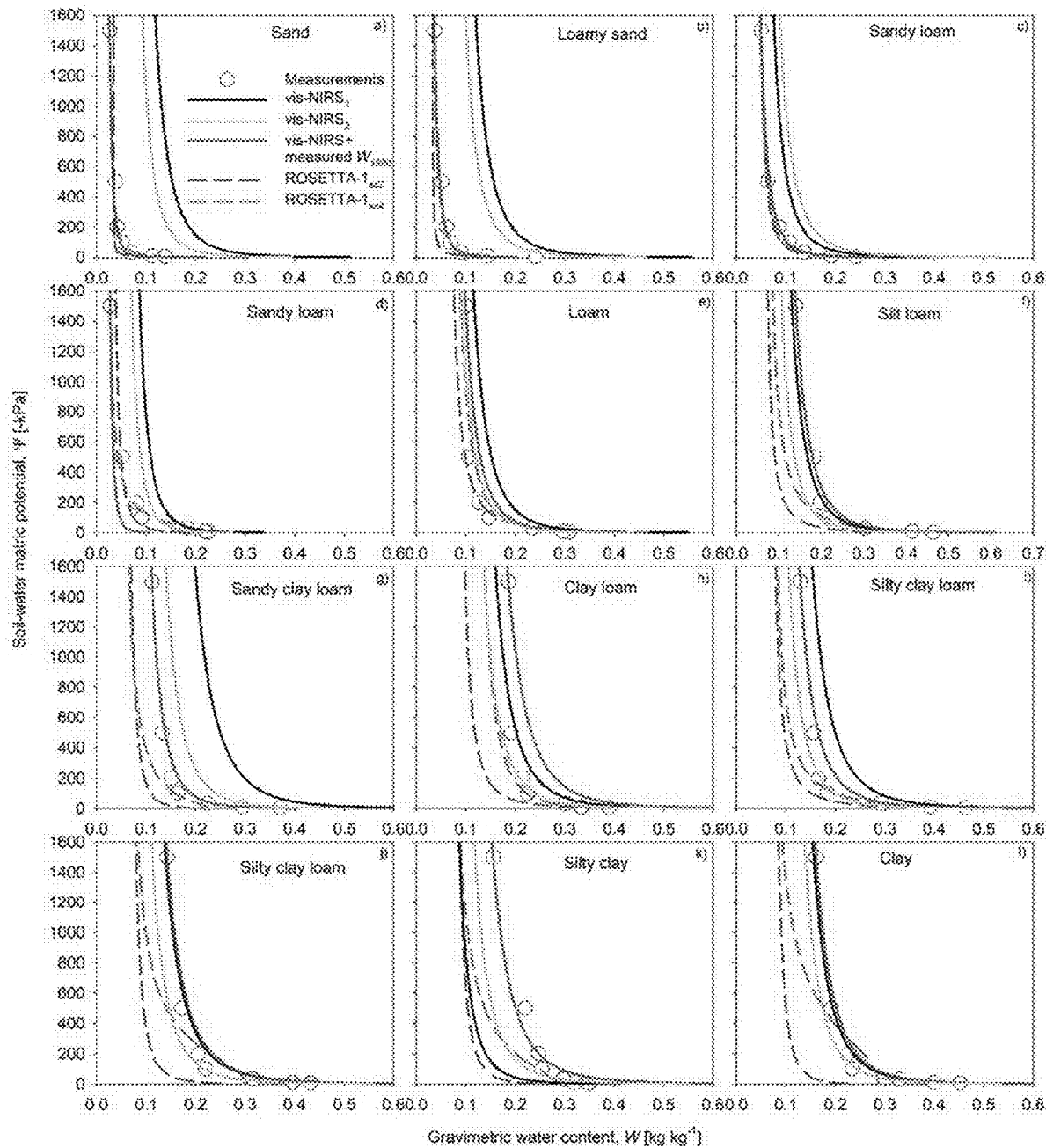
FIG. 7 shows, for multiple textural classes, respective plots a)-i) of predictive performance of soil-water retention curve using the visible-near-infrared (vis-NIRS) spectroscopy built on a small (vis-NIRS$_1$) and a larger (vis-NIRS$_2$) library, vis-NIRS and measured gravimetric water content at −1500 kPa (vis-NIRS+measured $W_{1500}$), ROSETTA-1 scenario 2 (ROSETTA-$1_{sc2}$), and ROSETTA-1 scenario 4 (ROSETTA-$1_{sc4}$) for 12 soil samples from different textural classes. Circles indicate the soil-water retention measurements at seven matric potentials.

The obtained predicted parameters of each scenario, i.e., $W_{1500}$ and Campbell b for the vis-NIRS, θr, θs, α, and n for ROSETTA-$1_{sc2}$ and ROSETTA-$1_{sc4}$, were then inserted into the anchored Campbell soil-water retention function (vis-NIRS scenarios) and van Genuchten (ROSETTA-1) and the SWRCs from near saturation (−2 kPa) up to −1600 kPa were obtained. The predictive performance of SWRC for 12 soil samples (at least one soil sample from each textural class) using the five scenarios, is illustrated in FIG. 6. It is observed that all scenarios of the vis-NIRS predicted SWRC had a similar shape with the soil-water retention measurements. However, for the sand (FIG. 7a), loamy sand (FIG. 7b), and sandy clay loam (FIG. 7g) the vis-NIRS$_1$ predicted SWRCs have presented higher gravimetric water contents at the given matric potentials, while the vis-NIRS$_1$ and vis-NIRS$_1$ predicted gravimetric water contents for the silty clay soil (FIG. 7k) were lower than the measured contents. The vis-NIRS$_1$ predicted SWRC for the remaining soils were compared closely with the measurements. The SWRC obtained from the vis-NIRS$_2$ were compared closely with the measured data except for the sand, loamy sand, and silty clay (FIGS. 7a, b, k).

Comparing the two scenarios of the ROSETTA-1, it is observed that the SWRCs derived from scenario-4 were better predicted in horizontal shift compared to scenario-2 but not in shape. Specifically, for the sandy clay loam (FIG. 5g), silty clay loam (FIG. 7j), silty clay (FIG. 7k), and clay (FIG. 7l), the predicted SWRCs derived from the scenario-4 could not predict the wetter end. The predicted SWRC obtained from the R vis-NIRS+measured $W_{1500}$ were better predicted compared to the other four scenarios for all the soil samples except for the sandy loam (FIG. 7d), loam (FIG. 7e), and clay loam (FIG. 7h).

The Campbell SWRC was selected in particular for this example, because it can accurately fit the measured soil-water retention data, although other examples can use other known SWRCs. Moreover, the parameter of the Campbell b was found to be directly related to the clay contents and organic matter, which can be predicted from vis-NIRS with high accuracy. Furthermore, the saturated water content is poorly related to the vis-NIRS, and water contents at drier points can be predicted from basic soil properties such as for clay. Therefore, under the disclosed method, the parameters of the modified anchored Campbell SWRC can be very well predicted from vis-NIRS.

As noted above, a variety of SWRCs can be used in other examples. However, the Campbell SWRC may be particularly suitable for some applications. For example, a widely used function is the van Genuchten SWRC, which has four parameters that need to be estimated (θs, θr, α, and n). However, a is directly related to the inverse of air-entry pressure which is substantially varied even within a soil textural class and it would probably be poorly predicted from the vis-NIRS.

The measurements of the soil-water retention curve were based on sieved soil samples. Measurements on undisturbed columns would allow to include in the calibration models the structure of the soil as well since undisturbed samples retain the in-situ properties of the soil.

Spectral measurement peaks near 1400 and 1900 nm indicate the presence of water molecules, and if molecular water is present, these two features always appear (Hunt, 1977). At 2200 nm the peak is because of the combination of the OH stretch with the fundamental Al—OH bending mode (Hunt, 1977). In the visible range the peaks could be assigned to organic matter (Galvao and Vitorello, 1998; Viscarra Rossel et al., 2006) and iron oxide minerals (Hunt, 1977). Additionally, peaks around 1400 nm can be attributed to the 1$^{st}$ overtone of the structural O—H stretching mode and a combination of vibrations of water bound in the interlayer lattices as hydrated cations and adsorbed water on particle surfaces (Bishop et al., 1994). In the region of 2200 to 2500 nm, there can be a combination of vibrations including O—H stretching and metal-OH bends (Stenberg et al., 2010). The minerals and organic components of soil are indirectly related to the $W_{1500}$ and Campbell b since these are linked with the clay and carbon contents and thus, the peaks in the visible and near-infrared range could be used for the development of calibration models for predicting the two parameters ($W_{1500}$, Campbell b).

The predictions for the $W_{1500}$ in the validation dataset were improved when the calibration model was based on a larger library, indicating that more soil samples in the calibration dataset led the calibration models to better capture the important peaks. Moreover, it was found that the highest values of the RMSE were in the sandier classes for both parameters regardless of the applied library. Notably, Blaschek et al. (2019) have found that the sand contents were poorly predicted from the vis-NIRS.

The statistics of the predicted SWRC of each soil textural class were improved when more soil samples were included in the calibration model of $W_{1500}$. However, the statistics obtained from the cross-validation for $W_{1500}$ of the larger database were slightly worst compared to those obtained from the small library. This is probably because more textural classes were included and simultaneously evaluated (e.g. sand, sandy clay, silty clay, and silt). Moreover, the range and the number of soil samples of the $W_{1500}$ for each class were larger.

The horizon-specific models have shown that a soil sample from topsoil could be predicted from a calibration model built on subsoils. However, the predictions of the subsoils based on a model built from topsoil did not yield sufficient predictive ability. A reason for that is because the topsoils were predicted from a larger database since the number of the subsoils was almost three times higher than the topsoils. Moreover, a subsoil consists of greater minerals and materials of iron and aluminum compounds than topsoil. These compounds are reflected in the vis-NIRS range and thus a model including only topsoils would not be expected to sufficiently predict parameters for subsoils.

Currently, there are few studies in the literature for predicting the SWRC. However, these studies have generally been based on a small number of classes of soils from limited geographic areas, did not recognize the value of the ranges of pF used herein for anchoring of SWRCs (and particularly relative to the Campbell function), and were not subject to rigorous validation. Further, at least one earlier study (Babaeian et al., 2015) has questioned the feasibility of some aspects of the methods disclosed herein, relative to a wide range of soil classes. In this regard, for example Babaeian et al. (2015) and Santra et al. (2009) developed spectral models for predicting the van Genuchten parameters. Specifically, Babaeian et al. (2015) developed point and parametric spectral transfer functions to predict soil water contents at nine specific soil matric potentials (from saturation up to −1500 kPa), and the parameters of van Genuchten and Brooks-Corey soil-water retention functions. The soil samples included in the calibration models were derived from an area from Iran, were topsoils, and varied within a specific soil texture range (e.g., clay: 15-45, sand: 13-63, silt contents: 21-52%). They have reported similar to this study $R^2$ (0.63) for the water content at −1500 kPa and the $R^2$ of van Genuchten and Brooks-Corey parameters varied from 0.14 to 0.44.

The vis-NIRS for all scenarios captured the shape of the SWRC, while the ROSETTA-1$_{sc4}$ failed for few soil samples since the predicted curve sharply reached the saturation degree at drier $\Psi$. Moreover, the vis-NIRS$_2$ yielded to better prediction for the wettest water contents. On the other hand, the vis-NIRS$_1$ and vis-NIRS$_2$ failed to predict the SWRC of the sandier soils compared to the ROSETTA-1 scenarios, and as it was discussed this is because of the poor predictability of the spectroscopy for the sandier soils. However, when a measured $W_{1500}$ was included, the predictions derived from the vis-NIS were equally good as with ROSETTA-1 and compared closely to the measured soil-water retention data. An advantage of the vis-NIRS is that only the knowledge of the spectral data is required to obtain the prediction of an SWRC without having the soil texture analysis and bulk density. Additionally, ROSETTA-1$_{sc4}$ required the knowledge of two volumetric water content at specific matric potential (−33, and −1500 kPa), while for the vis-NIRS+measured $W_{1500}$, a point approximately closed to that potential would be sufficient. However, the anchored Campbell SWR function should be anchored at the measured soil-water matric potential. Silva et al. (2021) have developed software namely Splintex 2.0 which is a PTF model developed with a user-friendly computer interface for estimating hydraulic functions' parameters. They have also compared their model development with the predictions obtained from ROSETTA and have found comparable results with ROSETTA with lower RMSE values of the volumetric water content in ROSETTA. Furthermore, Wösten et al. (2001) and Pachepsky et al. (2001) found that differences from 0.06 up to 0.11 in the volumetric water contents are acceptable.

Thus, the method demonstrated by this study could be applied for obtaining a rapid estimation of the SWRC. Specifically, a small amount of air-dried, and sieved soil sample needed to be scanned in a spectrometer and within few seconds the parameters of the anchored Campbell soil-water retention function could be obtained. Because of the rapidity and low cost of the proposed method, the estimation of the SWRCs could be at a high spatial resolution and thus could assist in modeling and forecasting in different disciplines such as hydrogeology, environmental geosciences. In this regard, some embodiments of the disclosed technology can generally include devices (e.g., hand-held or other portable devices) that can receive soil samples, obtain relevant spectroscopic data, and then determine relevant SWRCs for the soil samples according to the general principles discussed above. For example, hand-held spectrometers, or spectrometers mounted on probes (e.g., push probes) or on mobile platforms (e.g., ground vehicles, drones, satellites, manned aircraft, etc.) can be used to acquire spectroscopic data in some embodiments. Further, in these and other examples, soil samples may not necessarily be processed as described above (or at all). Correspondingly, some embodiments may be particularly efficient for large-area, in-field analysis.

In summary, this example thus demonstrates that vis-NIRS can be used as a tool to predict an SWRC from the near saturation (−2 kPa) up to −1500 kPa for different soil textural classes. More specifically, this example demonstrates in particular the unexpected result that the Campbell soil-water retention function, anchored at −1500 kPa or lower can be characterized with substantial accuracy for a particular soil sample based on the use of vis-NIRS to determine the Campbell b and $W_{1500}$. In particular, it is concluded that: Vis-NIRS can be used for predicting the SWRC and for capturing the shape of the SWRC. Further, by adding a measured $W_{1500}$, the predictive performance of the SWRC was increased even for sandy soils.

REFERENCES

Babaeian, E. et al., 2015. A comparative study of multiple approaches for predicting the soil-water retention curve: hyperspectral information vs. basic soil properties. Soil Sci Soc Am J, 79(4): 1043-1058. DOI:10.2136/ss-saj2014.09.0355

Barnes, R. J., Dhanoa, M. S., Lister, S. J., 1989. Standard normal variate transformation and de-trending of near-infrared diffuse reflectance spectra. Appl Spectrosc, 43(5): 772-777. DOI:10.1366/0003702894202201

Bishop, J. L., Pieters, C. M., Edwards, J. O., 1994. Infrared spectroscopic analyses on the nature of water in montmorillonite. Clay Clay Miner, 42(6): 702-716. DOI: 10.1346/CCMN.1994.0420606

Blaschek, M., Roudier, P., Poggio, M., Hedley, C. B., 2019. Prediction of soil available water-holding capacity from visible near-infrared reflectance spectra. Sci Rep-Uk, 9(1): 12833-12833. DOI:10.1038/s41598-019-49226-6

Brooks, R. H. and Corey, A. T., 1964. Hydraulic properties of porous media. Hydrology Paper no. 3. Civil Engineering Dep., Colorado State Univ., Fort Collins, CO.

Campbell, G., Shiozawa, S., 1992. Prediction of hydraulic properties of soils using particle-size distribution and bulk density data. Indirect methods for estimating the hydraulic properties of unsaturated soils: 317-328.

Campbell, G. S., 1974. Simple method for determining unsaturated conductivity from moisture retention data. Soil Science, 117(6): 311-314. DOI:10.1097/00010694-197406000-00001

Clapp, R. B., Hornberger, G. M., 1978. Empirical equations for some soil hydraulic-properties. Water Resour Res, 14(4): 601-604. DOI:10.1029/WR014i004p00601 de Jong, S., 1993. Simpls—an alternative approach to partial least-squares regression. Chemometr Intell Lab, 18(3): 251-263. DOI:10.1016/0169-7439(93)85002-X Galvao, L. S., Vitorello, I., 1998. Variability of laboratory measured soil lines of soils from southeastern Brazil. Remote Sens Environ, 63(2): 166-181. DOI:10.1016/S0034-4257(97)00135-1

Gowen, A. A., Downey, G., Esquerre, C., O'Donnell, C. P., 2011. Preventing over-fitting in PLS calibration models of near-infrared (NIR) spectroscopy data using regression coefficients. J Chemometr, 25(7): 375-381. DOI:10.1002/cem.1349

Gupta, S. C., Larson, W. E., 1979. Estimating soil-water retention characteristics from particle-size distribution, organic-matter percent, and bulk-density. Water Resour Res, 15(6): 1633-1635. DOI:10.1029/WR015i006p01633

Hunt, G. R., 1977. Spectral signatures of particulate minerals in visible and near infrared. Geophysics, 42(3): 501-513. DOI:10.1190/1.1440721

Jarvis, N. J., Messing, I., Larsson, M. H., Zavattaro, L., 1999. Measurement and prediction of near-saturated hydraulic conductivity for use in dual-porosity models, In: van Genuchten, M. T., Leij, F. J., Wu, L. (Eds.). Characterization and measurement of the hydraulic properties of unsaturated porous media (Riverside, CA, USA: Oct. 22-24, 1997), pp. 839-850.

Jensen, D. K., Tuller, M., de Jonge, L. W., Arthur, E., Moldrup, P., 2015. A new two-stage approach to predicting the soil water characteristic from saturation to oven-dryness. J Hydrol, 521: 498-507. DOI:10.1016/j.jhydrol.2014.12.018

Karup, D., Moldrup, P., Tuller, M., Arthur, E., de Jonge, L. W., 2017. Prediction of the soil water retention curve for structured soil from saturation to oven-dryness. Eur J Soil Sci, 68(1): 57-65. DOI:10.1111/ejss.12401

Kilmer, V. J., Alexander, L. T., 1949. Methods of making mechanical analyses of soils. Soil Science, 68(1): 15-24. DOI:10.1097/00010694-194907000-00003

Klute, A., 1986. Water retention: Laboratory methods. In A. Klute (ed.) Methods of soil analysis. Part 1. Physical and mineralogical methods. 2nd ed. Agron. Monogr. 9. ASA and SSSA, Madison, WI, 5: 635-662.

Mader, D. L., 1963. Soil Variability-A Serious Problem in Soil-Site Studies in the Northeast. Soil Science Society of America Journal, 27(6): 707-709. DOI:10.2136/sssaj1963.03615995002700060040x McDowell, M. L., Bruland, G. L., Deenik, J. L., Grunwald, S., Knox, N. M., 2012. Soil total carbon analysis in Hawaiian soils with visible, near-infrared and mid-infrared diffuse reflectance spectroscopy. Geoderma, 189-190: 312-320. DOI:10.1016/j.geoderma.2012.06.009

Moldrup, P., Olesen, T., Komatsu, T., Schjonning, P., Rolston, D. E., 2001. Tortuosity, diffusivity, and permeability in the soil liquid and gaseous phases. Soil Sci Soc Am J, 65(3): 613-623. DOI:10.2136/sssaj2001.653613x Nielsen, D. R., Biggar, J. W., Erh, K. T., 1973. Spatial variability of field-measured soil-water properties. Hilgardia, 42: 215-259. DOI:10.3733/hilg.v42n07p215

Norris, K., 2001. Applying norris derivatives. Understanding and correcting the factors which affect diffuse transmittance spectra. NIR news, 12(3): 6-9. DOI:10.1255/nirn.613

Olesen, T., Moldrup, P., Henriksen, K., Petersen, L. W., 1996. Modeling diffusion and reaction in soils 0.4. New models for predicting ion diffusivity. Soil Science, 161 (10): 633-645. DOI:10.1097/00010694-199610000-00001

Or, D., Tuller, M., 1999. Liquid retention and interfacial area in variably saturated porous media: Upscaling from single-pore to sample-scale model. Water Resour Res, 35(12): 3591-3605. DOI:10.1029/1999wr900262

Oswin, C. R., 1946. The kinetics of package life. III. The isotherm. Journal of the Society of Chemical Industry, 65(12): 419-421. DOI:10.1002/jctb.5000651216

Pachepsky, Y., Rawls, W. J., Giménez, D., 2001. Comparison of soil water retention at field and laboratory scales. Soil Sci Soc Am J, 65(2): 460-462. DOI:10.2136/sssaj2001.652460x Peck, A. J., Luxmoore, R. J., Stolzy, J. L., 1977. Effects of spatial variability of soil hydraulic properties in water budget modeling. Water Resources Research, 13(2): 348-354. DOI:10.1029/WR013i002p00348

Pham, H. Q., Fredlund, D. G., 2008. Equations for the entire soil-water characteristic curve of a volume change soil. Can Geotech J, 45(4): 443-453. DOI:10.1139/T07-117

Pittaki-Chrysodonta, Z. et al., 2019. Comparing visible-near-infrared spectroscopy and a pedotransfer function for predicting the dry region of the soil-water retention curve. Vadose Zone J, 18(1). DOI:10.2136/vzj2018.09.0180

Pittaki-Chrysodonta, Z., Hartemink, A. E., Sanderman, J., Ge, Y., Huang, J., 2021. Evaluating three calibration transfer methods for predictions of soil properties using mid-infrared spectroscopy. Soil Sci Soc Am J, n/a(n/a). DOI:10.1002/saj2.20225

Pittaki-Chrysodonta, Z. et al., 2018. Predicting the Campbell soil water retention function: Comparing visible-near-infrared spectroscopy with classical pedotransfer function. Vadose Zone J, 17(1). DOI:10.2136/vzj2017.09.0169

Rawls, W. J., Brakensiek, D. L., Saxton, K. E., 1982. Estimation of soil water properties. T Asae, 25(5). DOI: 10.13031/2013.33720

Rinnan, Å., Berg, F.v.d., Engelsen, S. B., 2009. Review of the most common pre-processing techniques for near-infrared spectra. TrAC Trends in Analytical Chemistry, 28(10): 1201-1222. DOI:10.1016/j.trac.2009.07.007

Rossi, C., Nimmo, J. R., 1994. Modeling of soil-water retention from saturation to oven dryness. Water Resour Res, 30(3): 701-708. DOI:10.1029/93wr03238

Santra, P. et al., 2009. Estimation of soil hydraulic properties using proximal spectral reflectance in visible, near-infrared, and shortwave-infrared (VIS-NIR-SWIR) region. Geoderma, 152(3-4): 338-349. DOI:10.1016/j.geoderma.2009.07.001

Savitzky, A., Golay, M. J. E., 1964. Smoothing and differentiation of data by simplified least squares procedures. Anal Chem, 36(8): 1627-1639. DOI:10.1021/ac60214a047

Schaap, M. G., Leij, F. J., van Genuchten, M. T., 1998. Neural network analysis for hierarchical prediction of soil hydraulic properties. Soil Sci Soc Am J, 62(4): 847-855. DOI:10.2136/sssaj1998.03615995006200040001x Schaap, M. G., Leij, F. J., van Genuchten, M. T., 2001. ROSETTA: a computer program for estimating soil hydraulic parameters with hierarchical pedotransfer functions. J Hydrol, 251(3): 163-176. DOI:10.1016/S0022-1694(01)00466-8

Seybold, C. A. et al., 2019. Application of mid-infrared spectroscopy in soil survey. Soil Sci Soc Am J, 83(6): 1746-1759. DOI:10.2136/sssaj2019.06.0205

Sharma, M. L., Uehara, G., 1968. Influence of soil structure on water relations in low humic latosols. I. Water retention. Soil Sci Soc Am Pro, 32(6): 765-&. DOI:10.2136/sssaj1968.03615995003200060021x Silva, A. C. d., Armindo, R. A., Minasny, B., Prevedello, C. L., 2021. Evaluating the Splintex model for estimating the soil water retention curve for a wide range of soils. Soil and Tillage Research, 209: 104974. DOI:10.1016/j.still.2021.104974

Sjöblom, J., Svensson, O., Josefson, M., Kullberg, H., Wold, S., 1998. An evaluation of orthogonal signal correction applied to calibration transfer of near infrared spectra. Chemometr Intell Lab, 44(1): 229-244. DOI:10.1016/S0169-7439(98)00112-9

Staff, S. S., 2014. Kellogg soil survey laboratory methods manual, USDA-NRCS, Washington, DC.

Stenberg, B., Rossel, R. A. V., Mouazen, A. M., Wetterlind, J., 2010. Visible and near infrared spectroscopy in soil science. Adv Agron, 107: 163-215. DOI:10.1016/S0065-2113(10)07005-7 van den Berg, C., Bruin, S., 1981. Water activity and its estimation in food systems: theoretical aspects. In: Rockland, L. B., Stewart, G. F. (Eds.), Water activity: Influences on food quality. Academic Press, New York, pp. 147-177.

van Genuchten, M. T., 1980. A closed-form equation for predicting the hydraulic conductivity of unsaturated soils. Soil Science Society of America Journal, 44(5): 892-898. DOI:10.2136/sssaj1980.03615995004400050002x Varvaris, I., Borgesen, C. D., Kjærgaard, C., Iversen, B. V., 2018. Three two-dimensional approaches for simulating the water flow dynamics in a heterogeneous tile-drained agricultural field in Denmark. Soil Science Society of America Journal, 82(6): 1367-1383. DOI:10.2136/sssaj2018.05.0190

Varvaris, I., Pittaki-Chrysodonta, Z., Borgesen, C. D., Iversen, B. V., 2020. Parameterization of two-dimensional approaches in HYDRUS-2D. Part 1: for simulating water flow dynamics in catchment scale. In review. Soil Science Society of America Journal.

Varvaris, I., Pittaki-Chrysodonta, Z., Moldrup, P., De Jonge, L. W., Iversen, B. V., 2019. Combining visible-near-infrared and pedotransfer functions for parameterization of tile drain flow simulations. Vadose Zone Journal, 18(1). DOI:10.2136/vzj2018.09.0171

Viscarra Rossel, R. A., Walvoort, D. J. J., McBratney, A. B., Janik, L. J., Skjemstad, J. O., 2006. Visible, near infrared, mid infrared or combined diffuse reflectance spectroscopy for simultaneous assessment of various soil properties. Geoderma, 131(1/2): 59-75. DOI:10.1016/j.geoderma.2005.03.007

Wetterlind, J., Stenberg, B., Viscarra Rossel, R. A., 2013. Soil analysis using visible and near infrared spectroscopy. Methods in molecular biology (Clifton, N.J.), 953: 95-107. DOI:10.1007/978-1-62703-152-3_6

Williams, J., Prebble, R. E., Williams, W. T., Hignett, C. T., 1983. The influence of texture, structure and clay mineralogy on the soil-moisture characteristic. Aust J Soil Res, 21(1): 15-32. DOI:10.1071/Sr9830015

Williams, J., Ross, P., Bristow, K. L., 1989. Prediction of the Campbell water retention function from texture, structure, and organic matter, In: van Genuchten, M Th. and Leij, F J (eds.). Proceedings of the International Workshop on Indirect Methods for Estimating the Hydraulic Properties of Unsaturated Soils (Riverside, CA, USA: Oct. 11-13, 1989), pp. 427-441.

Wood, E. F., Sivapalan, M., Beven, K., Band, L., 1988. Effects of spatial variability and scale with implications to hydrologic modeling. Journal of Hydrology, 102(1): 29-47. DOI:10.1016/0022-1694(88)90090-X Wösten, J. H. M., Pachepsky, Y. A., Rawls, W. J., 2001. Pedotransfer functions: bridging the gap between available basic soil data and missing soil hydraulic characteristics. J Hydrol, 251(3): 123-150. DOI:10.1016/S0022-1694(01)00464-4

TABLES

TABLE 1

General statistics of the gravimetric water content at −1500 kPa ($W_{1500}$) and Campbell b for the calibration and validation datasets of each textural class.

| Textural class | Dataset Statistics | Calibration | | | | Validation | |
|---|---|---|---|---|---|---|---|
| | | Small | | Large | | | |
| | | $W_{1500}$ | Campbell b | $W_{1500}$ | | $W_{1500}$ | Campbell b |
| Sand ($N_{cal1}$, $N_{cal2}$, $N_{val}$: 4, 124, 1)[1] | Mean | 0.023 | 6.16 | 0.022 | | 0.026 | 3.31 |
| | Median | 0.023 | 6.41 | 0.017 | | 0.026 | 3.31 |
| | Q1 | 0.020 | 5.07 | 0.009 | | | |
| | Q3 | 0.026 | 7.50 | 0.027 | | N/A | N/A |
| | σ | 0.006 | 1.71 | 0.021 | | | |
| | skew | 0.233 | −0.44 | 2.358 | | | |
| | Min | 0.016 | 4.11 | 0.001 | | 0.026 | 3.31 |
| | Max | 0.030 | 7.71 | 0.133 | | 0.026 | 3.31 |
| | Min-Max | 0.016-0.03 | 4.11-7.71 | 0.001-0.133 | | 0.026-0.026 | 3.31-3.31 |
| Loamy sand ($N_{cal1}$, $N_{cal2}$, $N_{val}$: 11, 105, 5) | Mean | 0.031 | 3.00 | 0.050 | | 0.032 | 3.15 |
| | Median | 0.030 | 2.97 | 0.039 | | 0.032 | 3.08 |
| | Q1 | 0.021 | 2.62 | 0.027 | | 0.029 | 3.04 |
| | Q3 | 0.041 | 3.12 | 0.048 | | 0.037 | 3.15 |
| | σ | 0.013 | 0.51 | 0.056 | | 0.007 | 0.24 |
| | skew | 0.142 | 1.51 | 5.458 | | −0.467 | 1.67 |
| | Min | 0.013 | 2.41 | 0.009 | | 0.022 | 2.94 |
| | Max | 0.054 | 4.25 | 0.488 | | 0.040 | 3.56 |
| | Min-Max | 0.013-0.054 | 2.41-4.25 | 0.009-0.488 | | 0.022-0.04 | 2.94-3.56 |

TABLE 1-continued

General statistics of the gravimetric water content at −1500 kPa ($W_{1500}$) and
Campbell b for the calibration and validation datasets of each textural class.

| | Dataset | Calibration | | | Validation | |
| --- | --- | --- | --- | --- | --- | --- |
| | | Small | | Large | | |
| Textural class | Statistics | $W_{1500}$ | Campbell b | $W_{1500}$ | $W_{1500}$ | Campbell b |
| Sandy loam ($N_{cal1}$, $N_{cal2}$, $N_{val}$: 78, 311, 35) | Mean | 0.062 | 3.46 | 0.074 | 0.051 | 3.16 |
| | Median | 0.060 | 3.25 | 0.059 | 0.055 | 3.17 |
| | Q1 | 0.052 | 3.06 | 0.047 | 0.045 | 2.90 |
| | Q3 | 0.069 | 3.63 | 0.080 | 0.063 | 3.45 |
| | σ | 0.015 | 0.79 | 0.060 | 0.016 | 0.48 |
| | skew | 0.655 | 3.63 | 4.754 | −0.617 | −0.31 |
| | Min | 0.028 | 2.71 | 0.002 | 0.018 | 2.08 |
| | Max | 0.108 | 8.41 | 0.598 | 0.080 | 4.21 |
| | Min-Max | 0.028-0.108 | 2.71-8.41 | 0.002-0.598 | 0.018-0.08 | 2.08-4.21 |
| Loam ($N_{cal1}$, $N_{cal2}$, $N_{val}$: 32, 208, 15) | Mean | 0.096 | 3.99 | 0.105 | 0.115 | 4.23 |
| | Median | 0.087 | 3.80 | 0.095 | 0.103 | 3.76 |
| | Q1 | 0.075 | 3.59 | 0.076 | 0.092 | 3.39 |
| | Q3 | 0.095 | 4.04 | 0.117 | 0.125 | 4.34 |
| | σ | 0.037 | 0.91 | 0.053 | 0.039 | 1.27 |
| | skew | 2.180 | 3.67 | 3.152 | 0.951 | 1.42 |
| | Min | 0.051 | 3.08 | 0.025 | 0.056 | 3.03 |
| | Max | 0.208 | 8.30 | 0.515 | 0.190 | 7.03 |
| | Min-Max | 0.051-0.208 | 3.08-8.3 | 0.025-0.515 | 0.056-0.19 | 3.03-7.03 |
| Silt loam ($N_{cal1}$, $N_{cal2}$, $N_{val}$: 15, 175, 10) | Mean | 0.124 | 3.53 | 0.111 | 0.124 | 3.47 |
| | Median | 0.097 | 3.51 | 0.100 | 0.124 | 3.40 |
| | Q1 | 0.080 | 3.23 | 0.073 | 0.096 | 3.00 |
| | Q3 | 0.146 | 3.75 | 0.132 | 0.138 | 3.87 |
| | σ | 0.065 | 0.70 | 0.066 | 0.044 | 0.59 |
| | skew | 1.351 | 0.70 | 2.652 | 0.323 | 0.42 |
| | Min | 0.057 | 2.47 | 0.013 | 0.056 | 2.66 |
| | Max | 0.285 | 5.04 | 0.510 | 0.204 | 4.51 |
| | Min-Max | 0.057-0.285 | 2.47-5.04 | 0.013-0.51 | 0.056-0.204 | 2.66-4.51 |
| Sandy clay loam ($N_{cal1}$, $N_{cal2}$, $N_{val}$: 37, 103, 13) | Mean | 0.099 | 3.98 | 0.107 | 0.101 | 4.13 |
| | Median | 0.096 | 3.95 | 0.102 | 0.107 | 4.13 |
| | Q1 | 0.086 | 3.61 | 0.091 | 0.091 | 3.94 |
| | Q3 | 0.108 | 4.29 | 0.117 | 0.114 | 4.33 |
| | σ | 0.020 | 0.48 | 0.026 | 0.017 | 0.37 |
| | skew | 2.056 | 0.44 | 1.086 | −0.407 | −0.32 |
| | Min | 0.068 | 3.18 | 0.035 | 0.070 | 3.42 |
| | Max | 0.185 | 5.30 | 0.208 | 0.131 | 4.68 |
| | Min-Max | 0.068-0.185 | 3.18-5.3 | 0.035-0.208 | 0.07-0.131 | 3.42-4.68 |
| Sandy clay ($N_{cal1}$, $N_{cal2}$, $N_{val}$: 3, 14, 1) | Mean | 0.140 | 6.41 | 0.161 | 0.132 | 5.22 |
| | Median | 0.139 | 6.66 | 0.148 | 0.132 | 5.22 |
| | Q1 | 0.136 | 6.10 | 0.135 | | |
| | Q3 | 0.144 | 6.84 | 0.170 | N/A | N/A |
| | σ | 0.008 | 0.76 | 0.040 | | |
| | skew | 0.722 | −1.31 | 1.471 | | |
| | Min | 0.133 | 5.55 | 0.118 | 0.132 | 5.22 |
| | Max | 0.149 | 7.02 | 0.259 | 0.132 | 5.22 |
| | Min-Max | 0.133-0.149 | 5.55-7.02 | 0.118-0.259 | 0.132-0.132 | 5.22-5.22 |
| Clay loam ($N_{cal1}$, $N_{cal2}$, $N_{val}$: 12, 104, 4) | Mean | 0.169 | 5.58 | 0.155 | 0.131 | 5.76 |
| | Median | 0.167 | 5.50 | 0.148 | 0.128 | 5.74 |
| | Q1 | 0.142 | 4.74 | 0.128 | 0.114 | 4.70 |
| | Q3 | 0.190 | 6.53 | 0.178 | 0.145 | 6.81 |
| | σ | 0.036 | 1.01 | 0.055 | 0.043 | 1.25 |
| | skew | 0.401 | −0.08 | 0.400 | 0.379 | 0.01 |
| | Min | 0.120 | 4.19 | 0.004 | 0.081 | 4.65 |
| | Max | 0.226 | 6.85 | 0.346 | 0.186 | 6.92 |
| | Min-Max | 0.12-0.226 | 4.19-6.85 | 0.004-0.346 | 0.081-0.186 | 4.65-6.92 |
| Silty clay loam ($N_{cal1}$, $N_{cal2}$, $N_{val}$: 10, 130, 3) | Mean | 0.157 | 5.06 | 0.154 | 0.137 | 4.50 |
| | Median | 0.160 | 4.79 | 0.153 | 0.139 | 4.73 |
| | Q1 | 0.145 | 4.62 | 0.134 | 0.134 | 4.36 |
| | Q3 | 0.166 | 5.38 | 0.173 | 0.141 | 4.76 |
| | σ | 0.014 | 0.82 | 0.048 | 0.007 | 0.44 |
| | skew | −0.298 | 0.78 | 1.656 | −1.152 | −1.71 |
| | Min | 0.132 | 3.98 | 0.006 | 0.129 | 3.99 |
| | Max | 0.177 | 6.43 | 0.456 | 0.143 | 4.78 |
| | Min-Max | 0.132-0.177 | 3.98-6.43 | 0.006-0.456 | 0.129-0.143 | 3.99-4.78 |
| Silty clay ($N_{cal1}$, $N_{cal2}$, $N_{val}$: 2, 89, 1) | Mean | 0.260 | 5.71 | 0.210 | 0.155 | 7.19 |
| | Median | 0.260 | 5.71 | 0.198 | 0.155 | 7.19 |
| | Q1 | 0.209 | 5.55 | 0.173 | | |
| | Q3 | 0.311 | 5.87 | 0.230 | N/A | N/A |
| | σ | 0.144 | 0.45 | 0.076 | | |
| | skew | N/A | N/A | 1.633 | | |

TABLE 1-continued

General statistics of the gravimetric water content at −1500 kPa ($W_{1500}$) and
Campbell b for the calibration and validation datasets of each textural class.

| | | Calibration | | | Validation | |
|---|---|---|---|---|---|---|
| | Dataset | Small | | Large | | |
| Textural class | Statistics | $W_{1500}$ | Campbell b | $W_{1500}$ | $W_{1500}$ | Campbell b |
| | Min | 0.158 | 5.39 | 0.042 | 0.155 | 7.19 |
| | Max | 0.362 | 6.03 | 0.557 | 0.155 | 7.19 |
| | Min-Max | 0.158-0.362 | 5.39-6.03 | 0.042-0.557 | 0.155-0.155 | 7.19-7.19 |
| Clay | Mean | 0.284 | 6.06 | 0.228 | 0.183 | 5.55 |
| ($N_{cal1}$, $N_{cal2}$, | Median | 0.282 | 5.94 | 0.219 | 0.161 | 5.35 |
| $N_{val}$: 11, 132, | Q1 | 0.259 | 5.79 | 0.180 | 0.160 | 5.27 |
| 3) | Q3 | 0.317 | 6.49 | 0.267 | 0.195 | 5.73 |
| | σ | 0.045 | 0.64 | 0.068 | 0.040 | 0.49 |
| | skew | −0.167 | −0.64 | 0.384 | 1.721 | 1.51 |
| | Min | 0.210 | 4.74 | 0.052 | 0.158 | 5.19 |
| | Max | 0.356 | 6.97 | 0.422 | 0.229 | 6.11 |
| | Min-Max | 0.21-0.356 | 4.74-6.97 | 0.052-0.422 | 0.158-0.229 | 5.19-6.11 |
| Silt | Mean | | | 0.047 | | |
| ($N_{cal1}$, $N_{cal2}$, | Median | N/A | | 0.054 | N/A | |
| $N_{val}$: —, 7, —) | Q1 | | | 0.023 | | |
| | Q3 | | | 0.060 | | |
| | σ | | | 0.025 | | |
| | skew | | | 0.295 | | |
| | Min | | | 0.021 | | |
| | Max | | | 0.085 | | |
| | Min-Max | | | 0.021-0.085 | | |
| Not defined | Mean | | | 0.165 | | |
| ($N_{cal1}$, $N_{cal2}$, | Median | N/A | | 0.118 | N/A | |
| $N_{val}$: — 65, —) | Q1 | | | 0.061 | | |
| | Q3 | | | 0.236 | | |
| | σ | | | 0.132 | | |
| | skew | | | 1.023 | | |
| | Min | | | 0.005 | | |
| | Max | | | 0.590 | | |
| | Min-Max | | | 0.005-0.59 | | |
| Total | Mean | 0.100 | 4.05 | 0.116 | 0.088 | 3.82 |
| ($N_{cal1}$, $N_{cal2}$, | Median | 0.083 | 3.73 | 0.098 | 0.080 | 3.55 |
| $N_{val}$: 215, | Q1 | 0.060 | 3.22 | 0.056 | 0.054 | 3.14 |
| 1567, 91) | Q3 | 0.115 | 4.44 | 0.158 | 0.117 | 4.19 |
| | σ | 0.065 | 1.16 | 0.084 | 0.047 | 1.07 |
| | skew | 1.829 | 1.40 | 1.494 | 0.723 | 1.43 |
| | Min | 0.013 | 2.41 | 0.001 | 0.018 | 2.08 |
| | Max | 0.362 | 8.41 | 0.598 | 0.229 | 7.19 |
| | Min-Max | 0.013-0.362 | 2.41-8.41 | 0.001-0.598 | 0.018-0.229 | 2.08-7.19 |

TABLE 2

Statistical characteristics of the predicted gravimetric water content
at −1500 kPa ($W_{1500}$) and Campbell b derived from the cross-validation
(A) and validation (B) datasets for each soil textural class.

A: Calibration dataset

| Soil parameter | $W_{1500}$-Small library | | | $W_{1500}$-Large library Statistic | | | Campbell b | | |
|---|---|---|---|---|---|---|---|---|---|
| Textural class | $R^2$ | Bias | RMSE | $R^2$ | Bias | RMSE | $R^2$ | Bias | RMSE |
| Sand | | N/A | | 0.45 | 0.046 | 0.061 | | N/A | |
| Loamy sand | 0.02 | 0.010 | 0.031 | 0.42 | 0.032 | 0.057 | 0.62 | 0.271 | 0.565 |
| Sandy loam | 0.02 | 0.019 | 0.033 | 0.29 | 0.019 | 0.054 | 0.44 | 0.196 | 0.625 |
| Loam | 0.65 | −0.012 | 0.026 | 0.28 | −0.001 | 0.046 | 0.47 | −0.180 | 0.678 |
| Silt loam | 0.40 | −0.023 | 0.055 | 0.40 | −0.009 | 0.053 | 0.00 | 0.349 | 0.933 |
| Sandy clay loam | 0.07 | −0.003 | 0.073 | 0.23 | 0.019 | 0.039 | 0.29 | 0.069 | 1.427 |
| Sandy clay | | N/A | | 0.21 | 0.023 | 0.043 | | N/A | |
| Clay loam | 0.55 | −0.035 | 0.049 | 0.49 | −0.010 | 0.043 | 0.03 | −0.932 | 1.446 |
| Silty clay loam | 0.51 | −0.014 | 0.044 | 0.32 | −0.029 | 0.050 | 0.09 | −0.384 | 0.834 |

TABLE 2-continued

Statistical characteristics of the predicted gravimetric water content at −1500 kPa ($W_{1500}$) and Campbell b derived from the cross-validation (A) and validation (B) datasets for each soil textural class.

| | | | | | | | | | |
|---|---|---|---|---|---|---|---|---|---|
| Silty clay | | N/A | | 0.15 | −0.040 | 0.086 | | N/A | |
| Clay | 0.32 | −0.043 | 0.057 | 0.23 | −0.036 | 0.073 | 0.02 | −0.256 | 0.820 |
| Silt | | N/A | | 0.64 | 0.040 | 0.071 | | N/A | |
| Not defined | | | | 0.59 | −0.023 | 0.088 | | | |
| All soil samples | 0.64 | 0.000 | 0.039 | 0.52 | 0.000 | 0.058 | 0.56 | 0.000 | 0.769 |

B: Validation dataset

| Soil parameter | $W_{1500}$-Small dataset | | | $W_{1500}$-Large dataset Statistic | | | Campbell b | | |
|---|---|---|---|---|---|---|---|---|---|
| Textural class | $R^2$ | Bias | RMSE | $R^2$ | Bias | RMSE | $R^2$ | Bias | RMSE |
| Sand | | N/A | | | | | | N/A | |
| Loamy sand | 0.91 | 0.058 | 0.065 | 0.63 | 0.038 | 0.041 | 0.49 | 1.063 | 1.115 |
| Sandy loam | 0.10 | 0.041 | 0.051 | 0.37 | 0.028 | 0.034 | 0.01 | 0.725 | 1.048 |
| Loam | 0.49 | 0.026 | 0.039 | 0.14 | −0.018 | 0.039 | 0.24 | −0.057 | 1.078 |
| Silt loam | 0.53 | 0.009 | 0.031 | 0.69 | −0.022 | 0.036 | 0.73 | 0.487 | 0.566 |
| Sandy clay loam | 0.02 | 0.020 | 0.056 | 0.04 | 0.016 | 0.026 | 0.22 | 0.083 | 0.501 |
| Sandy clay | | N/A | | | | | | N/A | |
| Clay loam | | | | | | | | | |
| Silty clay loam | | | | | | | | | |
| Silty clay | | | | | | | | | |
| Clay | | | | | | | | | |
| All soil samples | 0.34 | 0.027 | 0.049 | 0.49 | 0.008 | 0.035 | 0.19 | 0.306 | 1.009 |

TABLE 3

Statistical characteristics of the predicted gravimetric water content at −1500 kPa ($W_{1500}$) and Campbell b derived from the topsoils and subsoils for each soil textural class based on a small dataset.

A: Topsoils

| Soil parameter | $W_{1500}$ | | | Campbell b Statistic | | |
|---|---|---|---|---|---|---|
| Textural class | $R^2$ | Bias | RMSE | $R^2$ | Bias | RMSE |
| Sand (—) | | N/A | | | N/A | |
| Loamy sand (N = 3) | | | | | | |
| Sandy loam (N = 53) | 0.02 | 0.025 | 0.035 | 0.27 | 0.525 | 0.639 |
| Loam (N = 19) | 0.09 | 0.014 | 0.046 | 0.27 | 0.289 | 1.043 |
| Silt loam (N = 8) | 0.52 | −0.013 | 0.051 | 0.01 | 0.544 | 0.759 |
| Sandy clay loam (N = 8) | 0.09 | 0.030 | 0.049 | 0.70 | 0.518 | 0.675 |
| Sandy clay (—) | | N/A | | | N/A | |
| Clay loam (N = 3) | | | | | | |
| Silty clay loam (—) | | | | | | |
| Silty clay (—) | | | | | | |
| Clay (N = 4) | | | | | | |
| All (N = 97) | 0.49 | 0.016 | 0.042 | 0.55 | 0.390 | 0.791 |

B: Subsoils

| Soil parameter | $W_{1500}$ | | | Campbell b Statistic | | |
|---|---|---|---|---|---|---|
| Textural class | $R^2$ | Bias | RMSE | $R^2$ | Bias | RMSE |
| Sand (N = 5) | | N/A | | | N/A | |
| Loamy sand (N = 13) | 0.21 | 0.042 | 0.070 | 0.45 | −0.070 | 0.895 |
| Sandy loam (N = 60) | 0.02 | 0.031 | 0.060 | 0.19 | 0.065 | 1.017 |
| Loam (N = 28) | 0.06 | 0.030 | 0.050 | 0.58 | −0.755 | 0.952 |
| Silt loam (N = 17) | 0.50 | 0.013 | 0.037 | 0.16 | −0.096 | 0.741 |
| Sandy clay loam (N = 42) | 0.01 | −0.052 | 0.067 | 0.12 | 0.116 | 1.067 |
| Sandy clay (N = 4) | | N/A | | | N/A | |
| Clay loam (N = 13) | 0.02 | −0.036 | 0.088 | 0.17 | −1.208 | 1.532 |

TABLE 3-continued

Statistical characteristics of the predicted gravimetric water content at −1500 kPa ($W_{1500}$) and Campbell b derived from the topsoils and subsoils for each soil textural class based on a small dataset.

| Silty clay loam (N = 13) | 0.15 | −0.040 | 0.049 | 0.45 | −0.577 | 0.818 |
| Silty clay (N = 3) | | N/A | | | N/A | |
| Clay (N = 11) | 0.08 | −0.139 | 0.160 | 0.52 | −0.543 | 0.906 |
| All (N = 209) | 0.05 | −0.007 | 0.073 | 0.37 | −0.226 | 1.075 |

A: Topsoils

| Soil parameter | $W_{1500}$ | | | Campbell b | | |
|---|---|---|---|---|---|---|
| | Statistic | | | | | |
| Textural class | $R^2$ | Bias | RMSE | $R^2$ | Bias | RMSE |
| Sand (—) | | N/A | | | N/A | |
| Loamy sand (N = 3) | | | | | | |
| Sandy loam (N = 53) | 0.02 | 0.025 | 0.035 | 0.27 | 0.525 | 0.639 |
| Loam (N = 19) | 0.09 | 0.014 | 0.046 | 0.27 | 0.289 | 1.043 |
| Silt loam (N = 8) | 0.52 | −0.013 | 0.051 | 0.01 | 0.544 | 0.759 |
| Sandy clay loam (N = 8) | 0.09 | 0.030 | 0.049 | 0.70 | 0.518 | 0.675 |
| Sandy clay (—) | | N/A | | | N/A | |
| Clay loam (N = 3) | | | | | | |
| Silty clay loam (—) | | | | | | |
| Silty clay (—) | | | | | | |
| Clay (N = 4) | | | | | | |
| All (N = 97) | 0.49 | 0.016 | 0.042 | 0.55 | 0.390 | 0.791 |

B: Subsoils

| Soil parameter | $W_{1500}$ | | | Campbell b | | |
|---|---|---|---|---|---|---|
| | Statistic | | | | | |
| Textural class | $R^2$ | Bias | RMSE | $R^2$ | Bias | RMSE |
| Sand (N = 5) | | N/A | | | N/A | |
| Loamy sand (N = 13) | 0.21 | 0.042 | 0.070 | 0.45 | −0.070 | 0.895 |
| Sandy loam (N = 60) | 0.02 | 0.031 | 0.060 | 0.19 | 0.065 | 1.017 |
| Loam (N = 28) | 0.06 | 0.030 | 0.050 | 0.58 | −0.755 | 0.952 |
| Silt loam (N = 17) | 0.50 | 0.013 | 0.037 | 0.16 | −0.096 | 0.741 |
| Sandy clay loam (N = 42) | 0.01 | −0.052 | 0.067 | 0.12 | 0.116 | 1.067 |
| Sandy clay (N = 4) | | N/A | | | N/A | |
| Clay loam (N = 13) | 0.02 | −0.036 | 0.088 | 0.17 | −1.208 | 1.532 |
| Silty clay loam (N = 13) | 0.15 | −0.040 | 0.049 | 0.45 | −0.577 | 0.818 |
| Silty clay (N = 3) | | N/A | | | N/A | |
| Clay (N = 11) | 0.08 | −0.139 | 0.160 | 0.52 | −0.543 | 0.906 |
| All (N = 209) | 0.05 | −0.007 | 0.073 | 0.37 | −0.226 | 1.075 |

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A method of characterizing soil comprising:
   receiving, with one or more computing devices, data for a soil sample comprising visible-near infrared (vis-NIR) spectroscopy data;
   determining a first model parameter for a Campbell soil-water retention function and a second model parameter for the Campbell soil-water retention function using a model calibrated on vis-NIR spectroscopy data from a plurality of soil samples, wherein the first model parameter and the second model parameter are determined by the model using a common input comprising the received vis-NIR spectroscopy data; and
   characterizing the soil sample based on the soil-water retention function
   wherein the first model parameter provides an anchor value for the soil-water retention curve, wherein the second model parameter is an exponential shape factor; and
   wherein the anchor value corresponds to a water potential of potential force (pF) at least between 3.8 and 4.2, inclusive.

2. The method of claim 1, wherein the anchor value corresponds to a water potential of pF at least 4.2.

3. The method of claim 1, further comprising:
receiving a soil sample that is not processed and is obtained from the field, wherein the water content of the received sample is about the same as the water content of the sample when it was obtained from the field; and
conducting a spectroscopy analysis of the soil sample to obtain the spectroscopy data.

4. The method of claim 3, wherein the spectroscopy analysis includes vis-NIR spectroscopy analysis.

5. The method of claim 3, wherein soil sample is an air-dried, sieved soil sample.

6. The method of claim 3, wherein soil sample is a core sample.

7. The method of claim 1, wherein the first model parameter is determined with the one or more computing devices based on the spectroscopy data.

8. The method of claim 1, wherein the vis-NIR spectroscopy data comprises spectroscopy data in the spectral range of 350-2500 nm (nanometers).

9. The method of claim 1, wherein the plurality of soil samples comprises at least one sample from each of the following textural classes: loamy sand, sandy loam, loam, silt loam, silt, sandy clay loam, clay loam, silty clay loam, sandy clay, silty clay, or clay.

10. The method of claim 1, wherein the model comprises a partial least squares (PLS) model.

11. A system for characterizing soil, the system comprising:
a spectrophotometer configured to receive a soil sample and provide spectroscopy data for the soil sample; and
one or more computing devices configured to:
receive the spectroscopy data for the soil sample from the spectrophotometer, wherein the spectroscopy data comprises visible-near infrared (vis-NIR) spectroscopy data;
determine a first model parameter for a Campbell soil-water retention function and a second model parameter for the Campbell soil-water retention function using a model calibrated on vis-NIR spectroscopy data from a plurality of soil samples, wherein the first model parameter and the second model parameter are determined by the model using a common input comprising the received vis-NIR spectroscopy data, the first model parameter providing an anchor value for the soil-water retention curve that corresponds to a water potential of potential force (pF) at least 3.8 and the second model parameter is an exponential shape factor; and
characterize the soil sample based on the Campbell soil-water retention function.

12. The system of claim 11, wherein the soil-water retention function is a modified anchored Campbell soil-water retention function.

13. The system of claim 12, wherein the anchor value corresponds to a water potential of pF at least 4.0.

14. The system of claim 11, wherein the spectrophotometer is configured for vis-NIR spectroscopy analysis and the spectroscopy data is vis-NIR data.

15. The system of claim 11, wherein the first model parameter is determined based on the spectroscopy data and wherein the second model parameter is predictive of clay content and organic matter.

16. A method for characterizing soil at a sample site, the method comprising:
receiving into a spectrophotometer device, at the sample site, a soil sample from the sample site;
analyzing the soil sample, with a spectrophotometer of the spectrophotometer device to provide spectroscopy data comprising visible-near infrared (vis-NIR) spectroscopy data for the soil sample, and
with one or more computing devices of the spectrophotometer device, based on the spectroscopy data and a soil model accessed by the spectrophotometer device, determining a first model parameter for a Campbell soil-water retention function anchored at potential force (pF) at least 3.8 or at pF at least 4.2 and a second model parameter for the Campbell soil-water retention function, wherein the second model parameter is an exponential shape factor, thereby characterizing the soil sample based on the soil-water retention function, the soil model being determined based on spectroscopy data acquired from a plurality of other soil samples wherein the first model parameter and the second model parameter are determined by the model using a common input comprising the received vis-NIR spectroscopy data.

17. The method of claim 16, wherein the soil sample is not sieved, not ground, and not oven dried.

18. The method of claim 16, wherein the soil sample is classified as one or more of loamy sand, sandy loam, loam, silt loam, silt, sandy clay loam, clay loam, silty clay loam, sandy clay, silty clay, or clay.

* * * * *

UNITED STATES PATENT AND TRADEMARK OFFICE
CERTIFICATE OF CORRECTION

PATENT NO. : 12,405,213 B2
APPLICATION NO. : 17/833543
DATED : September 2, 2025
INVENTOR(S) : Jingyi Huang et al.

Page 1 of 1

It is certified that error appears in the above-identified patent and that said Letters Patent is hereby corrected as shown below:

In the Specification

Column 3, Line 2, "(pa)" should be --$(\rho_d)$--.

Column 3, Line 6, "pa" should be --$\rho_d$--.

Column 4, Line 8, "(ti)" should be --$(\Psi)$--.

Column 5, Line 2, "3.84.2" should be --3.8-4.2--.

Column 12, Line 1, "(a)" should be --$(\sigma)$--.

Column 12, Line 31, "highest a values" should be --highest $\sigma$ values--.

Column 12, Line 58, "highest a is" should be --highest $\sigma$ is--.

Column 16, Line 21, "However, a is" should be --However, $\alpha$ is--.

Signed and Sealed this
Twenty-eighth Day of October, 2025

John A. Squires
*Director of the United States Patent and Trademark Office*